US010413515B2

(12) United States Patent
Nussinovitch et al.

(10) Patent No.: US 10,413,515 B2
(45) Date of Patent: Sep. 17, 2019

(54) LIQUID-CORE CAPSULES COMPRISING NON-CROSSLINKED ALGINATE

(71) Applicant: Yissum Research Development Company of the Hebrew University of Jerusalem Ltd., Jerusalem (IL)

(72) Inventors: Amos Nussinovitch, Rehovot (IL); Orit Dagan, Rehovot (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 129 days.

(21) Appl. No.: 15/540,276

(22) PCT Filed: Dec. 29, 2015

(86) PCT No.: PCT/IL2015/051264
§ 371 (c)(1),
(2) Date: Jun. 28, 2017

(87) PCT Pub. No.: WO2016/108234
PCT Pub. Date: Jul. 7, 2016

(65) Prior Publication Data
US 2018/0001291 A1    Jan. 4, 2018

Related U.S. Application Data

(60) Provisional application No. 62/097,740, filed on Dec. 30, 2014.

(51) Int. Cl.
*A61K 9/48* (2006.01)
*B01J 13/16* (2006.01)
(Continued)

(52) U.S. Cl.
CPC .......... *A61K 9/4866* (2013.01); *A61K 9/4816* (2013.01); *B01J 13/14* (2013.01);
(Continued)

(58) Field of Classification Search
None
See application file for complete search history.

(56) References Cited

U.S. PATENT DOCUMENTS 8,337,923 B2 * 12/2012 Coyne ................ A21D 2/00
426/326
2004/0266026 A1 * 12/2004 Amiji ................ A61K 9/0092
436/531
(Continued)

FOREIGN PATENT DOCUMENTS

DE    198 13 011 A1    10/1999
EP    1 063 201 A1    12/2000
(Continued)

OTHER PUBLICATIONS

Alhaique et al., (1996) Gellan in sustained release formulations: preparation of gel capsules and release studies. Biomaterials, 17(20), 1981-1986.
(Continued)

*Primary Examiner* — Clare M Perrin
(74) *Attorney, Agent, or Firm* — J.A. Lindeman & Co., PLLC; Jeffrey Lindeman; Sulay Jhaveri

(57) ABSTRACT

Provided are hydrocolloid core-shell capsules including a liquid core including a non-crosslinked alginate solution and a solid or semi-solid shell including a hydrocolloid other than alginate crosslinked with metal ions, which do not crosslink alginate. Further provided is a method for the preparation of the liquid-core capsules including non-crosslinked alginate. The subject matter further provides the use of the capsules, inter alia, in the water treatment technology.

20 Claims, 7 Drawing Sheets

(51) Int. Cl.
 C02F 1/28 (2006.01)
 B01J 13/22 (2006.01)
 B01J 13/14 (2006.01)
 A23L 33/10 (2016.01)
 C02F 101/20 (2006.01)
(52) U.S. Cl.
 CPC ............... *B01J 13/16* (2013.01); *B01J 13/22* (2013.01); *C02F 1/286* (2013.01); *A23L 33/10* (2016.08); *A23V 2002/00* (2013.01); *C02F 2101/20* (2013.01)

(56) References Cited

U.S. PATENT DOCUMENTS

2014/0127290 A1* 5/2014 He .................. C12N 11/04 424/451
2014/0271843 A1* 9/2014 Ma .................. A61K 9/0024 424/463

FOREIGN PATENT DOCUMENTS

GB 2 388 581 A 11/2003
WO 99/48479 A1 9/1999
WO 2013/119183 A1 8/2013

OTHER PUBLICATIONS

Al-Rub et al., (2004) Biosorption of nickel on blank alginate beads, free and immobilized algal cells. Process Biochemistry, 39(11), 1767-1773.
Arica et al., (2003) Ca-alginate as a support for Pb (II) and Zn (II) biosorption with immobilized Phanerochaete chrysosporium. Carbohydrate Polymers, 52(2), 167-174.
Bremond et al., (2010) Formation of liquid-core capsules having a thin hydrogel membrane: liquid pearls. Soft Matter, 6(11), 2484-2488.
El-Kamel et al., (2003) Alginate-diltiazem hydrochloride beads: optimization of formulation factors, in vitro and in vivo availability. Journal of microencapsulation, 20(2), 211-225.
Fatin-Rouge et al., (2006) Removal of some divalent cations from water by membrane-filtration assisted with alginate. Water Research, 40(6), 1303-1309.
Gavrilescu, (2004) Removal of heavy metals from the environment by biosorption. Engineering in Life Sciences, 4(3), 219-232.
Grasdalen et al., (1987) Gelation of gellan gum. Carbohydrate polymers, 7(5), 371-393.
Hashim et al., (2011) Remediation technologies for heavy metal contaminated groundwater. Journal of environmental management, 92(10), 2355-2388.
Hua et al., (2012) Heavy metal removal from water/wastewater by nanosized metal oxides: a review. Journal of Hazardous Materials, 211, 317-331.
Ibáñez et al., (2002) Potential of protonated alginate beads for heavy metals uptake. Hydrometallurgy, 64(2), 89-99.
Järup, (2003) Hazards of heavy metal contamination. British medical bulletin, 68(1), 167-182.
Lagoa et al., (2007) Evaluation of dry protonated calcium alginate beads for biosorption applications and studies of lead uptake. Applied biochemistry and biotechnology, 143(2), 115-128.

Lázaro et al., (2003) Heavy metal biosorption by gellan gum gel beads. Water research, 37(9), 2118-2126.
Lim et al., (1980) Microencapsulated islets as bioartificial endocrine pancreas. Science, 210(4472), 908-910.
Liu et al., (1999) Alginate-Pectin-Poly-L-lysine Particulate as a Potential Controlled Release Formulation. Journal of Pharmacy and Pharmacology, 51(2), 141-149.
Morris et al., (2012) Gelation of gellan—a review. Food Hydrocolloids, 28(2), 373-411.
Nussinovitch et al., (1998) Liquid-core hydrocolloid-oil capsules. In: Gums and Stabilizers for the Food Industry. Williams and Phillips (eds.); vol. 9, pp. 323-332. Cambridge: The Royal Society of Chemistry, UK.
Nussinovitch et al., (1996) Liquid-core hydrocolloid capsules. Food hydrocolloids, 10(1), 21-26.
Nussinovitch et al., (1997) Temperature stable liquid core hydrocolloid capsules. Food hydrocolloids, 11(2), 209-215.
Orive et al., (2006) Biocompatibility of alginate—poly-l-lysine microcapsules for cell therapy. Biomaterials, 27(20), 3691-3700.
Papageorgiou et al., (2006) Heavy metal sorption by calcium alginate beads from Laminaria digitata. Journal of Hazardous Materials, 137(3), 1765-1772.
Papageorgiou et al., (2008) Calcium alginate beads from Laminaria digitata for the removal of Cu+ 2 and Cd+ 2 from dilute aqueous metal solutions. Desalination, 224(1-3), 293-306.
Plazinski, (2012) Sorption of lead, copper, and cadmium by calcium alginate. Metal binding stoichiometry and the pH effect. Environmental Science and Pollution Research, 19(8), 3516-3524.
Schutzendubel et al., (2002) Plant responses to abiotic stresses: heavy metal-induced oxidative stress and protection by mycorrhization. Journal of experimental botany, 53(372), 1351-1365.
Shawky, (2011) Improvement of water quality using alginate/montmorillonite composite beads. Journal of Applied Polymer Science, 119(4), 2371-2378.
Singh et al., (2012) Effective removal of Cu 2+ ions from aqueous medium using alginate as biosorbent. Ecological engineering, 38(1), 119-124.
Stewart et al., (2009) Impacts of calcium-alginate density on equilibrium and kinetics of lead (II) sorption onto hydrogel beads. Colloid and Polymer Science, 287(9), 1033-1040.
Tam et al., (2011) Biocompatibility and physicochemical characteristics of alginate-polycation microcapsules. Acta biomaterialia, 7(4), 1683-1692.
Thu et al., (1996) Alginate polycation microcapsules: I. Interaction between alginate and polycation. Biomaterials, 17(10), 1031-1040.
Thu et al., (1996) Alginate polycation microcapsules: II. Some functional properties. Biomaterials, 17(11), 1069-1079.
Topuz et al., (2012) Magnesium ions and alginate do form hydrogels: a rheological study. Soft Matter, 8(18), 4877-4881.
Wong et al., (2011) Degradation of PEG and non-PEG alginate-chitosan microcapsules in different pH environments. Polymer degradation and stability, 96(12), 2189-2197.
Wu et al., (2010) Lanthanum adsorption using iron oxide loaded calcium alginate beads. Hydrometallurgy, 101(1), 76-83.
Zhang et al., (2011) Preparation and evaluation of alginate-chitosan microspheres for oral delivery of insulin. European Journal of Pharmaceutics and Biopharmaceutics, 77(1), 11-19.
Zhang et al., (2013) A novel core-shell microcapsule for encapsulation and 3D culture of embryonic stem cells. Journal of materials chemistry B, 1(7), 1002-1009.
CD-34, Gelrite® Gellan Gum for Microbiological Applications. CP Kelco U.S. Inc, Jun. 2007, 7 pages.

* cited by examiner

LIQUID-CORE CAPSULES COMPRISING NON-CROSSLINKED ALGINATE

FIELD OF THE INVENTION

The present invention is directed to hydrocolloid-based core-shell capsules comprising liquid alginate core and solid or semi-solid shell comprising a polymer other than alginate.

BACKGROUND OF THE INVENTION

Alginate is a naturally occurring polysaccharide composed of D-mannuronic acid (M block) and L-guluronic acid (G block). Alginate is derived from the cell wall of different species of brown algae. A unique property of alginate is that it forms a hydrogel under mild conditions. The major gelation mechanism in alginate is crosslinking of the polysaccharide carboxyl groups by positively charged metal cations [Nussinovitch, A., Hydrocolloid applications: gum technology in the food and other industries. Blackie Academic & Professional London, 1997]. Alginate has been extensively used for encapsulation and immobilization of various types of materials including, inter alia, inorganic ions, organic molecules (immobilization of microorganisms, encapsulation of hydrophilic and hydrophobic components) and living cells. Technological fields widely utilizing alginate are pharmacology, agriculture, food industry and water treatment. After dissolution alginate can be used to thicken (increase viscosity) of fluids (water). For example, propylene glycol alginate (PGA) increases the viscosity of many salad dressings, due to its stability in low pH.

A variety of hydrocolloids have been studied for their potential use as carriers for the controlled release of compounds, including drugs and agro-chemical compounds, such as those used for pest control. Several studies have focused on alginate-based carriers, revealing some difficulties. For one, the loading efficacy of the active ingredient (drug, agro-chemical compound) is too low due to its leakage into the cross-linking solution [El-Kamel A H, Al-Gohary O M N, Hosny E A. 2003, J Microencapsul 20(2):221-225; Liu P, Krishnan T R. 1999, J Pharm Pharmacol 51(2):141-149].

Alginate has also been one of the most commonly used biomaterials for cell encapsulation, probably due to its natural origin and excellent biocompatibility. The gelling property of alginate, has been utilized to prepare cell-loaded alginate beads by electrospray and microfluidic flow focusing. However, microbeads consisting solely of alginate were not sufficiently effective in protecting the encapsulated cells from being attacked by the host immune system. Therefore, polylysine (PLL) coated alginate microbeads and alginate-PLL-alginate or APA microcapsules were developed to allow further permeability control [F. Lim, A. M. Sun, Science, 210, 21, 1980, 908-910; G. Orive, S. K. Tam, J. L. Pedraz and J. P. Halle, Biomaterials, 2006, 27, 3691-3700; S. K. Tam, S. Bilodeau, J. Dusseault, G. Langlois, J. P. Halle and L. H. Yahia, Acta Biomater., 2011, 7, 1683-1692]. Alginate counteracts rudimental charges of chitosan, thereby providing a stable shell. However, APA microcapsules have a drawback of inducing inflammatory cytokine release from host immune cells.

Conventional treatment technologies for the removal of heavy metals from aqueous solutions are expensive and generate huge quantities of toxic chemical sludge [Shawky, H. A., 2011, Journal of Applied Polymer Science 119, 2371-2378]. Many different technologies aimed at mitigating the problem have been proposed, and can be classified into three major categories, including chemical treatments, such as precipitation and ion-exchange filters; biological treatments, specifically biosorption; and physical methods, such as, for example, adsorption and membrane filtration [Hashim, M., Mukhopadhyay, S., Sahu, J. N., Sengupta, B., Journal of environmental management 92, 2355-2388, 2011; Hua, M., Zhang, S., Pan, B., Zhang, W., Lv, L., Zhang, Q., Journal of Hazardous Materials 211, 317-331, 2012]. Another efficient alternative includes biotechnological processes based on polysaccharides' ability to adsorb heavy metals [Papageorgiou, S., Kouvelos, E., Katsaros, F., Desalination 224, 293-306, 2008; Hua et al., 2012].

Alginate may be used to eliminate metal ions from effluent via two possible mechanisms: the alginate can immobilize other types of heavy-metal adsorbents, or it can serve as the chelating agent itself [Plazinski, W., Environmental Science and Pollution Research 19, 3516-3524, 2012]. Under the latter mechanism, alginate is already partially crosslinked, mainly using calcium cations, and the heavy-metal cations are sequestered from the solution, bonding to the alginate's remaining free carboxyl groups or replacing some of the calcium cations [Singh, L., Pavankumar, A. R., Lakshmanan, R., Rajarao, G. K., Ecological Engineering 38, 119-124, 2012]. Lead-adsorption efficiency by calcium-alginate has been reported to be 240 mg $Pb^{2+}$/g [Stewart, T. J., Yau, J.-H., Allen, M. M., Brabander, D. J., Flynn, N. T., Colloid and Polymer Science 287, 1033-1040, 2009], 144 $Pb^{2+}$/g [Yakup Arica, M., Arpa, Ç, Ergene, A., Bayramoğlu, G., GenÇ Ö., Carbohydrate Polymers 52, 167-174, 2003] and 130 $Pb^{2+}$/g [Lagoa, R., Rodrigues, J., Applied biochemistry and biotechnology 143, 115-128, 2007].

Other hydrocolloid materials have also been studied for heavy metal absorption. The $Ni^{2+}$ accumulation in batch mode from diluted solutions by gel beads of gellan gum (GG), alginate, κ-carrageenan, agar, agarose, and two mixtures of GG+agar was investigated, where gel beads of GG were stable, easily obtainable and showed the highest $Ni^{2+}$ accumulation [Lázaro N1, Sevilla A L, Morales S, Marqués A M, Water Research 05/2003; 37(9):2118-26].

EP1063201 is directed to a method of removing harmful ions contained in water, such as copper, zinc, cadmium, chromium or lead, characterized in that an anionic group-containing hydrophilic polymeric substance is dispersed in said water in an undissolved state, and said harmful ions are insolubilized while maintaining said anionic group-containing hydrophilic polymeric substance in the undissolved state.

In all of the above technologies, alginate is typically used in a solid or semi-solid form, in which alginate is crosslinked by divalent metal cations, most commonly by calcium ions. To the best of the inventors' knowledge, no non-crosslinked alginate as a core within a liquid-core capsule, wherein the liquid-core capsule is produced in a one-step process, has been reported for use in water purification. Recently, liquid-core hydrocolloid capsules were reported for use in cell encapsulation. ACA capsules with liquid alginate core were produced by a multi-step process including forming conventional ACA solid beads and liquefying the alginate core [Zhang et al., 1002|J. Mater. Chem. B, 2013, 1, 1002-1009].

There remains an unmet need for the cost-effective, environmentally friendly and easily producible hydrocolloid-based materials for use in the removal of toxic heavy metals from aqueous media, drug encapsulation, and food and agricultural technology.

SUMMARY OF THE INVENTION

The present invention provides liquid-core hydrocolloid-based capsules, comprising a liquid alginate core. Liquid-core hydrocolloid capsules typically include a liquid encapsulated in a spherical polymeric membrane. The present invention is based in part on an unexpected finding that non-crosslinked alginate can be encapsulated in a solid or semi-solid shell composed of a hydrocolloid other than alginate, wherein the shell comprises metal ions, which do not crosslink alginate but are capable of crosslinking the hydrocolloid present therein. The present invention further provides a method of preparation of said core-shell hydrocolloid capsules, wherein said method is a cost-effective one-step process. The inventors have further discovered that the capsules comprising non-crosslinked alginate liquid core and a hydrocolloid membrane provided increased heavy-metal ion adsorption efficiency as compared to the currently known values for calcium-alginate. The capsules according to the principles of the present invention were further characterized by good compressive mechanical properties, such as stress and strain at failure, which allow practical use thereof in water treatment systems. The inventors have further found that the capsules can be repeatedly used in the water treatment, without significant decrease in the adsorption efficiency thereof.

According to a first aspect, the present invention provides a hydrocolloid core-shell capsule comprising a liquid core comprising a non-crosslinked alginate solution and a solid or semi-solid shell comprising a hydrocolloid other than alginate crosslinked with metal ions, which do not crosslink alginate. The hydrocolloid present in the shell is also termed herein "shell hydrocolloid".

In some embodiments, the metal ions are selected from magnesium ions, potassium ions and sodium ions. In further embodiments, the shell hydrocolloid is crosslinked with magnesium ions. In other embodiments, the shell hydrocolloid is crosslinked with potassium ions. In additional embodiments, the shell hydrocolloid is crosslinked with sodium ions.

In some embodiments, the shell consists essentially of the hydrocolloid other than alginate. In further embodiments, the shell is essentially free of alginate.

According to some embodiments, the alginate solution comprises alginic acid, an ester of alginic acid or an alginate salt. Each possibility represents a separate embodiment of the invention. The ester of alginic acid can include polypropylene glycol alginate (PGA). The alginate salt can be selected from the group consisting of sodium ($Na^+$) salts, potassium ($K^+$) salts, ammonium ($NH_4^+$) salts and combinations thereof.

In some embodiments, the concentration of the alginate solution ranges from about 1% w/w to about 10% w/w.

In some embodiments, the alginate solution has a concentration of calcium ions that is lower than about 0.01M. In further embodiments, the concentration of calcium ions is lower than about 0.005M. In still further embodiments, the concentration of calcium ions is lower than about 0.00109M.

The shell hydrocolloid can be selected from the group consisting of gellan, κ-carrageenan and a combination thereof. Each possibility represents a separate embodiment of the invention. In some exemplary embodiments, the shell hydrocolloid comprises gellan. In further exemplary embodiments, gellan is crosslinked with magnesium ions.

The concentration of magnesium ions, which crosslink the shell hydrocolloid can range from about 0.075 to about 0.5 mM/g(hydrocolloid). In certain embodiments, the concentration of magnesium ions, which crosslink the shell hydrocolloid ranges from about 0.1 to about 0.25 mM/g (hydrocolloid).

In some embodiments, gellan is crosslinked with potassium ions or sodium ions. Each possibility represents a separate embodiment of the invention.

In some embodiments, the shell hydrocolloid comprises κ-carrageenan. In further embodiments, κ-carrageenan is crosslinked with potassium ions. In certain such embodiments, the weight percent of potassium ions, which crosslink the shell hydrocolloid ranges from about 0.5% to about 1.5% of the total weight of the shell.

In some embodiments, the shell further comprises at least one surfactant. The surfactant can be selected from the group consisting of lecithin; sultaines CHAPS; cocamidopropyl hydroxysultaine; cocamidopropyl betaine; phosphatidylserine; phosphatidylethanolamine; phosphatidylcholine; sphingomyelin and combinations thereof. Each possibility represents a separate embodiment of the invention. In some exemplary embodiments, the surfactant comprises lecithin. In some embodiments, the surfactant is present in the shell in a concentration of from about 5 ppm to about 500 ppm.

In some embodiments, the shell further comprises a polycation. In some embodiments, the polycations is a polymer. In further embodiments, the polymer has a positively charged hydrophilic amino group. The polycation can be selected from the group consisting of poly-L-lysine (PLL), polyarginine, chitosan, and combinations thereof. Each possibility represents a separate embodiment of the invention. In certain embodiments, the polycation is a polymer having a molecular weight of less than about 50 kDa.

In some embodiments, the capsule is essentially spherical. In some embodiments, the aspect ratio of the capsule ranges from about 0.90 to about 1. In some embodiments, the diameter of the capsule ranges from about 50 μm to about 5 cm. In further embodiments, the diameter of the capsule ranges from about 1 mm to about 10 mm.

In some embodiments, the volume of the alginate solution ranges from about 100 microliter to about 1 ml. In some embodiments, the shell thickness ranges from about 0.2 mm to about 1.2 mm.

In some embodiments, the volume (v/v) ratio between the liquid alginate core and the shell ranges from about 0.4:1 to about 1.25:1.

In some embodiments, the capsule has a stress at failure ranging from about 10 kPa to about 40 kPa. In further embodiments, the capsule has a strain at failure ranging from about 0.45 to about 0.65. In some embodiments, the capsule is characterized by an adsorption capacity of lead cations of at least about 180 mg (lead)/g(alginate).

In another aspect there is provided a method for the preparation of a hydrocolloid core-shell capsule comprising a liquid core comprising a non-crosslinked alginate solution and a solid or semi-solid shell comprising a hydrocolloid other than alginate, the method comprising: (i) preparing a mixture of alginate ions and metal ions, which do not crosslink alginate and crosslink said hydrocolloid; (ii) providing a hydrocolloid solution, wherein the hydrocolloid is other than alginate; (iii) dripping the mixture of the alginate ions and metal ions into the hydrocolloid solution under constant mixing; and (iv) suspending the mixture formed in step (iii), thereby forming the hydrocolloid core-shell capsules.

In some embodiments, the metal ions are selected from magnesium ions, potassium ions and sodium ions. Each possibility represents a separate embodiment of the invention. In some exemplary embodiments, the metal ions are magnesium ions.

In some embodiments, the dripping in step (iii) is performed at a rate ranging from about 0.25 ml/sec to about 30 ml/sec. The constant mixing can be performed at a rate of 20 rpm to about 500 rpm. In some embodiments, the mixture is suspended in step (iv) for from about 0.1 to about 5 minutes.

The hydrocolloid can be selected from the group consisting of gellan, κ-carrageenan, and combinations thereof. Each possibility represents a separate embodiment of the invention. In some exemplary embodiments, the hydrocolloid is gellan.

According to some embodiments, the step of preparing a mixture of alginate ions and metal ions and comprises mixing a solution of alginate salt or alginic acid ester and a solution of metal salt. The alginate salt can be selected from the group consisting of sodium, potassium, ammonium salt and combinations thereof. In some embodiments, the mixture of alginate ions and metal ions comprises alginate salt or alginic acid ester in a weight percent ranging from about 1% to about 10% of the total weight of the mixture In some embodiments, the metal salt is a magnesium salt. The magnesium salt can be selected from the group consisting of a magnesium chloride, magnesium oxide, magnesium citrate, magnesium orotate, magnesium lactate, magnesium sulfate, magnesium carbonate and combinations thereof. Each possibility represents a separate embodiment of the invention. In certain embodiments, the magnesium salt is magnesium chloride. In certain embodiments, the mixture of alginate ions and metal ions comprises magnesium salt in the molar concentration of from about 0.25M to about 1.5M.

In some embodiments, the metal salt is a potassium salt. In some embodiments, the metal salt is a sodium salt.

In some embodiments, the mixture of alginate ions and metal ions has a temperature of from about 20° C. to about 30° C.

In some embodiments, the hydrocolloid is present in the hydrocolloid solution in a weight percent of from about 0.25% to about 0.75% of the total weight of the solution. In some embodiments, the hydrocolloid solution has a temperature of from about 25° C. to about 35° C.

In some embodiments, the density of the mixture of alginate ions and metal ions ranges from about 1.05 g/cm$^3$ to about 1.16 g/cm$^3$. In additional embodiments, the density of the hydrocolloid solution ranges from about 0.96 g/cm$^3$ to about 1.04 g/cm$^3$. In some embodiments, the viscosity of the mixture of alginate ions and metal ions ranges from about 600 cP to about 800 cP at 6.5 l/sec shear rate and temperature of about 25° C. In additional embodiments, the viscosity of the hydrocolloid solution ranges from about 5 cP to about 15 cP at 6.5 l/sec shear rate and temperature of about 30° C. In some embodiments, the surface tension of the mixture of alginate ions and metal ions ranges from about 35 to about 50 mN/m. In additional embodiments, the surface tension of the hydrocolloid solution ranges from about 65 to about 75 mN/m.

According to some embodiments, the hydrocolloid solution in step (ii) comprises a surfactant. The surfactant can be selected from the group consisting of lecithin; sultaines CHAPS (3-[(3-Cholamidopropyl)dimethylammonio]-1-propanesulfonate); cocamidopropyl hydroxysultaine; cocamidopropyl betaine; phosphatidylserine; phosphatidylethanolamine; phosphatidylcholine; sphingomyelin and combinations thereof. Each possibility represents a separate embodiment of the invention. In some exemplary embodiments, the surfactant comprises lecithin. The concentration of the surfactant can range from about 5 to about 500 ppm.

In some embodiments, the method comprises an additional step comprising contacting the capsules with a crosslinking agent or with a polycation. Each possibility represents a separate embodiment of the invention. Said contacting can be performed for from about 5 minutes to about 60 minutes. In certain embodiments, the crosslinking agent comprises magnesium ions. In further embodiments, the crosslinking agent comprises a solution of magnesium salt, such as, but not limited to, magnesium chloride. In certain embodiments, the solution of magnesium salt has a molar concentration of from about 0.1M to about 1.5M. The polycation can be selected from the group consisting of poly-L-lysine, polyarginine, chitosan, and combinations thereof. Each possibility represents a separate embodiment of the invention.

In some embodiments, the method further comprises the step of washing the capsules obtained in step (iv). In additional embodiments, the method comprises the step of washing the capsules obtained following the contacting with a crosslinking agent or with a polycation.

In some embodiments, there is provided a hydrocolloid core-shell capsule comprising a liquid core comprising a non-crosslinked alginate solution, wherein the capsule is prepared according to the method of the present invention.

The capsules according to the principles of the present invention are suitable for use in the water treatment, food industry, agriculture, medicine, pharmacology, biotechnology, and environmental applications. Each possibility represents a separate embodiment of the invention. In certain embodiments, the capsules are for use in the removal of heavy metal ions. In other embodiments, the capsules are for use in cell or drug encapsulation.

In another aspect there is provided a device comprising a plurality of capsules according to the principles of the present invention. In some embodiments, the plurality of capsules is immobilized within said device, said immobilization enabling flow of a liquid through the device. The device can further comprise a container, wherein the container comprises a sieve, an inlet, and an outlet, suitable for passing the liquid there through. In some embodiments, the sieve has pores which are smaller than the size of the capsules. In certain embodiments, the device is a filtering column.

In another aspect there is provided a method of removal of heavy metal ions from a liquid-containing environment, the method comprising bringing the capsules according to the principles of the present invention in contact with the liquid-containing environment, for a time and under conditions enabling entry and entrapment of the heavy metal ion into the capsules. In additional aspect there is provided a method of removal of heavy metal ions from a liquid-containing environment, the method comprising bringing the device according to the principles of the present invention in contact with the liquid-containing environment for a time and under conditions enabling entry and entrapment of the heavy metal ion into the capsules.

In some embodiments, the liquid-containing environment comprises water or moisture. Each possibility represents a separate embodiment of the invention.

The heavy metal ion can be selected from the group consisting of chromium, cobalt, nickel, copper, zinc, arsenic, selenium, silver, cadmium, antimony, mercury, thallium, lead ion and combinations thereof. Each possibility represents a separate embodiment of the invention.

In some embodiments, the method comprises regeneration of the capsules. Regeneration of the capsules can be performed by suspending the capsules in an acid. The acid can be selected from the group consisting of $HNO_3$, $H_2SO_4$, HCl, HI, HBr, $HClO_4$, and combinations thereof. The concentration of the acid can range from about 0.5M to about 2M. In certain embodiments, the capsules are suspended in the acid for from about 2 to about 48 hours. The regeneration procedure can further include a step of washing of the capsules until a neutral pH is reached. In some embodiments, the regeneration procedure further includes an additional step comprising contacting the capsules with a crosslinking agent. Said contacting can be performed for from about 5 minutes to about 60 minutes. In certain embodiments, the crosslinking agent comprises magnesium ions. In further embodiments, the crosslinking agent comprises a solution of magnesium salt, such as, but not limited to, magnesium chloride. In certain embodiments, the solution of magnesium salt has a molar concentration of from about 0.1M to about 1.5M. In some embodiments, the crosslinking agent comprises potassium ions or sodium ions. Each possibility represents a separate embodiment of the invention.

In some embodiments, the method includes multiple regenerations of the capsules. In certain embodiments, the step includes 1-3 regenerations of the capsules.

In some embodiments, the capsules retain at least about 80% of the initial heavy metal ion adsorption capacity thereof following regeneration. In further embodiments, the capsules retain at least about 50% of the initial heavy metal ion adsorption capacity thereof following multiple regenerations.

In some embodiments, the capsules retain at least about 60% of the stress value at failure following regeneration. In further embodiments, the capsules retain at least about 90% of the strain value at failure following regeneration.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

(FIG. 2A) 0.5 min; (FIG. 2B) 1 min; (FIG. 2C) 1.5 min; and (FIG. 2D) 2 min.

DETAILED DESCRIPTION OF THE INVENTION

Figure 1:
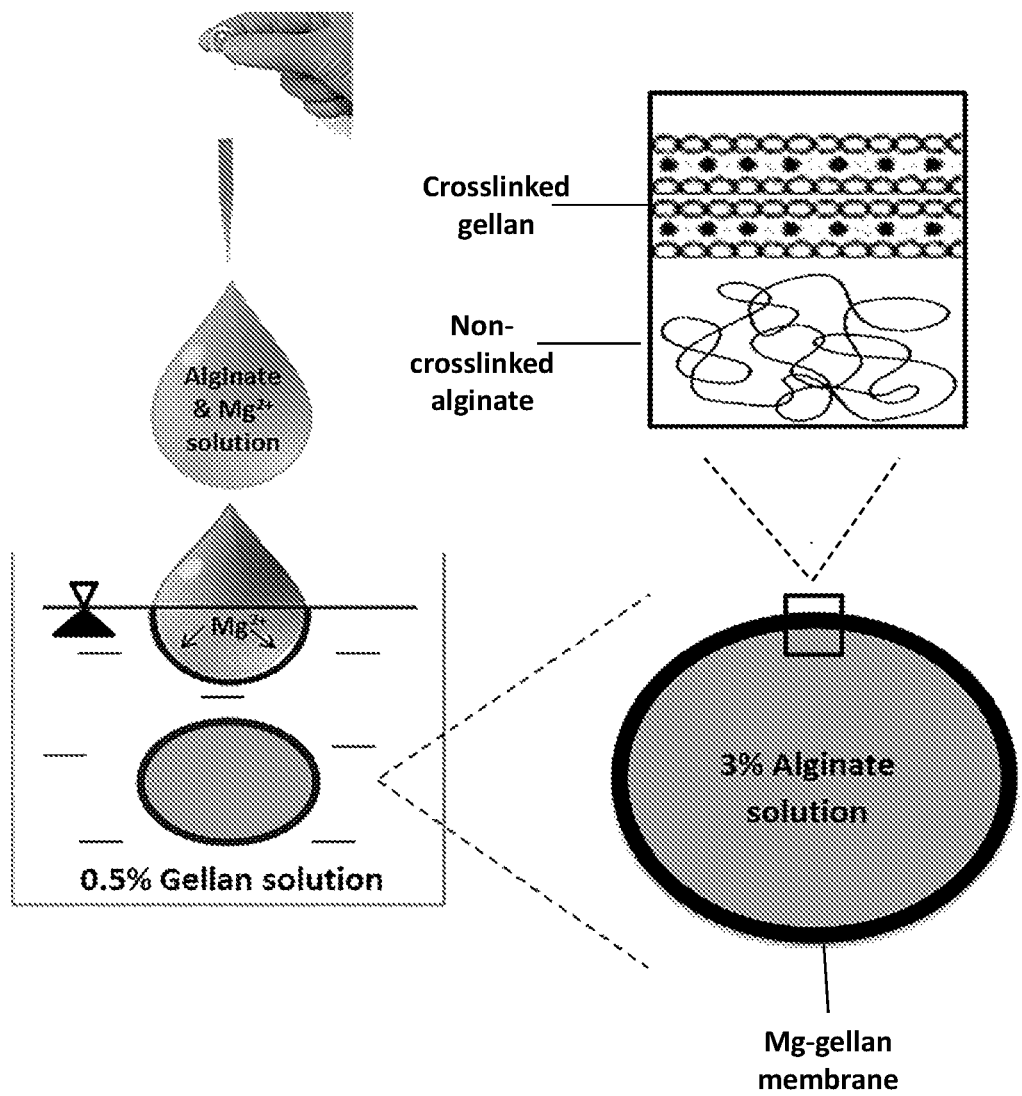
FIG. 1: Schematic presentation of the alginate-gellan liquid-core capsules' production. The liquid-core capsules comprise a non-crosslinked alginate core enclosed by a gellan-magnesium membrane. Dark circles (●) represent $Mg^{2+}$ ions.
Figure 2A:
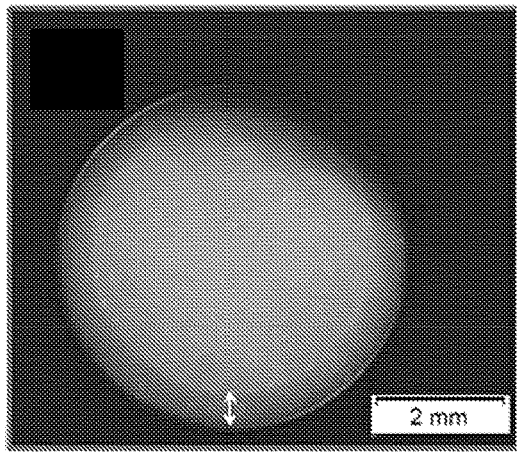
FIGS. 2A-2D: Gellan-alginate liquid-core capsules after different crosslinking durations.
Figure 2B:
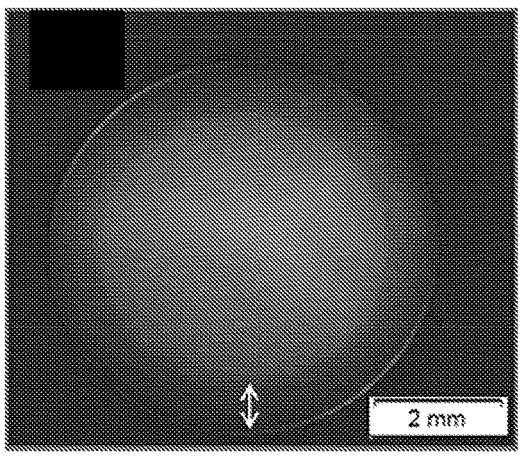
Figure 2C:
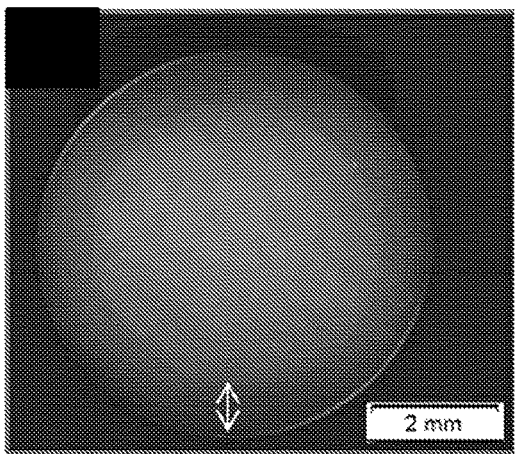
Figure 2D:
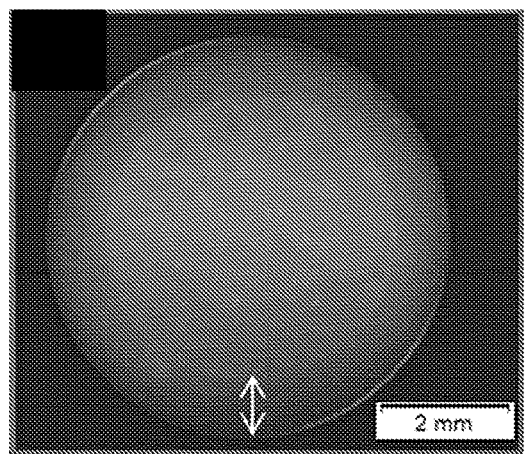

The present invention provides liquid-core hydrocolloid-based capsules, comprising a liquid alginate core. The alginate core is contained within a non-alginate polymer. The present invention is based in part on an unexpected finding that it is possible to produce a hydrocolloid-based capsule comprising a liquid alginate core and a polymer shell, wherein said polymer is other than alginate, using metal ions, which crosslink said polymer but do not crosslink alginate. Accordingly, the present invention provides for the first time a hydrocolloid-based capsule comprising a liquid alginate core and polymer shell comprising said metal ions, wherein the polymer is other than alginate. The hydrocolloid-based capsules of the present invention can be used in various technological fields, including, but not limited to, water treatment, agriculture, biotechnology, pharmacology, special medicinal purposes and for other environmental applications. Inventors have showed that liquid-alginate core capsules provided increased heavy-metal ion adsorption efficiency as compared to the currently known values for calcium alginate. Furthermore, the capsules of the present invention provided multiple cycles of heavy-metal ions removal, following a short regeneration process. The capsules were also characterized by high stress and strain resistivity. Thus, the hydrocolloid-based capsules of the present invention can beneficially be used in water-treatment systems, including filter columns. It has been discovered that the ion adsorption ability and mechanical properties can further be tuned by incorporation of an additional crosslinking agent, a shell-forming polymer or a surfactant into the polymer shell. The invention further provides a cost-effective, fast and convenient process for the preparation of the hydrocolloid-based alginate-core capsules. Various experimental conditions were tested and it was surprisingly found that precursor concentration and temperature had a pronounced effect on the formation of the capsules and properties thereof.

In a first aspect, there is provided a hydrocolloid core-shell capsule comprising a liquid core comprising a non-crosslinked alginate solution and a polymer membrane. The terms "membrane" and "shell" are used herein interchangeably.

Alginate, also termed herein algin, is an anionic polysaccharide distributed widely in the cell walls of brown algae, where through binding with water it forms a viscous gum. Alginate has a linear polymeric structure composed of D-mannuronic acid (M block) and L-guluronic acid (G block). Its colour ranges from white to yellowish-brown. It is sold in filamentous, granular or powdered forms.

Alginates are refined from brown seaweeds. A wide variety of brown seaweeds of the phylum Phaeophyceae are harvested throughout the world to be converted into the raw material commonly known as sodium alginate. Sodium alginate has a wide use across a wide variety of industries including food, textile printing and pharmaceutical. Alginate is both food and skin safe.

Alginates from different species of brown seaweed often have variations in their chemical structure, resulting in different physical properties. For example, some may yield an alginate that gives a strong gel, others yield a weaker gel; some alginates may readily give a cream/white alginate, others may give that only with difficulty and are best used for technical applications where color does not matter.

Commercial varieties of alginate are extracted from seaweed, including the giant kelp *Macrocystis pyrifera*, *Ascophyllum nodosum*, and various types of *Laminaria*. It is also produced by two bacterial genera *Pseudomonas* and *Azotobacter*. Bacterial alginates are useful for the production of micro- or nanostructures suitable for medical applications.

According to some embodiments, the alginate solution is selected from alginic acid, an ester of alginic acid, an alginate salt and combinations thereof. Each possibility represents a separate embodiment of the invention. The ester of alginic acid can include polypropylene glycol alginate (PGA). The alginate salt can be selected from the group consisting of sodium, potassium, and ammonium salts, and combinations thereof. Each possibility represents a separate embodiment of the invention. The chemical compound sodium alginate is the sodium salt of alginic acid. Its empirical formula is $NaC_6H_7O_6$. Sodium alginate is a gum, extracted from the cell walls of brown algae. Potassium alginate is a chemical compound that is the potassium salt of alginic acid. It is an extract of seaweed. Its empirical chemical formula is $KC_6H_7O_6$. In some exemplary embodiments, the alginate is sodium alginate.

In some embodiments, the alginate solution is an aqueous-based solution.

In some embodiments, the concentration of the alginate solution ranges from about 1% w/w to about 10% w/w. In further embodiments, the concentration of the alginate solution ranges from about 1% w/w to about 5% w/w. In still further embodiments, the concentration of the alginate solution ranges from about 2 to about 4% w/w. In some exemplary embodiments, the concentration of the alginate solution is about 3% w/w.

The alginate can include a low viscosity (LV) alginate or a high viscosity (HV) alginate. Each possibility represents a separate embodiment of the invention. The term "low viscosity alginate", as used herein, refers in some embodiments to an alginate solution having a viscosity of from about 4 cP to about 300 cP at the temperature of about 25° C., wherein the concentration of the alginate solution is about 1%-2% (w/w). The term "high viscosity alginate", as used herein, refers in some embodiments to an alginate solution having a viscosity of from about 400 cP to about 3000 cP at the temperature of about 25° C., wherein the concentration of the alginate solution is about 1%-2% (w/w). Without wishing to being bound by theory or mechanism of action, low viscosity alginate affords for the formation of alginate cores with higher alginate content. Without further wishing to being bound by theory or mechanism of action, high viscosity alginate can increase the mechanical resistance of the capsule. In some embodiments, the alginate includes PGA. It is further contemplated that PGA provides the capsule stability in acidic environments.

In some embodiments, the molecular weight of alginate ranges from about 30 to about 100 kDa. In further embodiments, the molecular weight of alginate ranges from about 40 to about 90 kDa. In yet further embodiments, the molecular weight of alginate ranges from about 50 to about 80 kDa. In some exemplary embodiments, the molecular weight of alginate ranges from about 60 to about 70 kDa.

The M:G (mannuronic acid:guluronic acid) ratio of alginate, suitable for the liquid core of the hydrocolloid-based capsules of the present invention can range from about 31:69 to about 65:35. In some exemplary embodiments, the M:G ratio of alginate is 61:39.

The term "non-crosslinked alginate" refers to an alginate that is not cross-linked by cations and/or by other positively charged hydrocolloids or polymers. Each possibility represents a separate embodiment of the invention. The non-crosslinked alginate is in a fluid form under regular room temperature and pressure and not in the form of gel or semi-solid, and the viscosity thereof is minimal. In some embodiments, the viscosity of the non-crosslinked alginate solution ranges from about 27 cP to 1500 cP at a temperature of 23.9° C.

In some embodiments, the alginate solution has a concentration of calcium ions that is lower than about 0.01M. In further embodiments, the concentration of calcium ions is lower than about 0.005M. In still further embodiments, the concentration of calcium ions is lower than about 0.00109M.

In some embodiments, the polymer present in the shell is water soluble. In further embodiments, the polymer is a hydrocolloid other than alginate. In some embodiments, the shell consists essentially of the hydrocolloid other than alginate. In further embodiments, the shell is essentially free of alginate. The term "essentially free of alginate", as used herein, refers in some embodiments, to a weight percent of alginate in the shell, which is lower than about 1% of the total weight of the shell. In further embodiments, the term refers to a weight percent of alginate, which is lower than about 0.5% of the total weight of the shell. In still further embodiments, the term refers to the weigh percent of alginate, which is lower than about 0.1% of the total weight of the shell. In yet further embodiments, the term refers to a weight percent of alginate, which is lower than about 0.05% of the total weight of the shell.

In some embodiments, the polymer forms a solid or a semi-solid shell around the alginate core. In alternative embodiments, the liquid alginate core is encapsulated within the solid or semi-solid polymer shell. The term "solid or semi-solid", as used herein, refers to a material having stress at failure of below about 15 kPa. Without wishing to being bound by theory or mechanism of action, the water soluble polymer suitable for the formation of the solid or semi-solid shell is a polymer, which is viscous and dense in a way that its viscosity and density must be higher than the viscosity and density of the alginate solution.

In some embodiments, the shell hydrocolloid is an anionic polysaccharide. In some embodiments, the anionic polysaccharide comprises at least one carboxylic group per repeating unit. In other embodiments, the anionic polysaccharide comprises at least one sulfate group per repeating unit.

The non-limiting examples of hydrocolloids suitable for the formation of the solid or semi-solid shell of the capsules of the present invention include gellan and k-carrageenan.

Gellan, also termed herein "gellan gum", is a water-soluble anionic polysaccharide produced by the bacterium *Sphingomonas elodea* (formerly *Pseudomonas elodea*). Gellan was initially identified as a substitute gelling agent at significantly lower use level to replace agar in solid culture media for the growth of various microorganisms.

The repeating unit of the polymer is a tetrasacharide, which consists of two residues of D-glucose and one of each residues of L-rhamnose and D-glucuronic acid. The tetrasacharide repeat has the following structure:

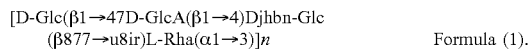

[D-Glc(β1→47D-GlcA(β1→4)Djhbn-Glc (β877→u8ir)L-Rha(α1→3)]n    Formula (1).

As evident from the formula, the tetrasacharide units are connected by (α1→3) glycosidic bonds.

Two types of gellan gum can be used in the shell of the hydrocolloid-based capsules of the present invention—low-acyl gellan gum and high-acyl gellan gum. Typically, gels made with low-acyl gellan gum tend to be brittle and firm, while gels made with high-acyl gellan gum are flexible and elastic. In some exemplary embodiments, gellan is a low acyl gellan gum Carrageenans are a family of linear sulphated high-molecular-weight polysaccharides that are extracted from red edible seaweeds. They are widely used in the food industry, for their gelling, thickening, and stabilizing properties. Carrageenans are large, highly flexible molecules that curl forming helical structures. This gives them the ability to form a variety of different gels at room temperature. The building blocks of carrageenans are repeating galactose units and 3,6 anhydrogalactose (3,6-AG) units, both sulfated and nonsulfated. The units are joined by alternating α-1,3 and β-1,4 glycosidic linkages.

There are three main varieties of carrageenan, which differ in their degree of sulphation. Kappa-carrageenan (also termed herein "k-carrageenan") has one sulphate group per disaccharide. Kappa-carrageenan forms strong, rigid gels in the presence of potassium ions. It is sourced mainly from *Kappaphycus alvarezii*.

In some embodiments, the shell hydrocolloid is gellan. In some embodiments, gellan is present in the solid or semi-solid shell in a weight percent ranging from about 0.2% to about 5% of the total weight of the shell. In further embodiments, gellan is present in the solid or semi-solid shell in a weight percent ranging from about 0.4% to about 4%. In still further embodiments, gellan is present in the solid or semi-solid shell in a weight percent ranging from about 0.6% to about 3%. In yet further embodiments, gellan is present in the solid or semi-solid shell in a weight percent ranging from about 0.8% to about 2%.

In some embodiments, the shell hydrocolloid is k-carrageenan. In some embodiments, k-carrageenan is present in the solid or semi-solid shell in a weight percent ranging from about 1% to about 5% of the total weight of the shell. In further embodiments, k-carrageenan is present in the solid or semi-solid shell in a weight percent ranging from about 2% to about 4%.

According to some embodiments, the solid or semi-solid shell comprises metal ions, which do not crosslink alginate and are capable of crosslinking the hydrocolloid present in the shell. The term "metal ions which do not crosslink alginate", as used herein, refers in some embodiments to metal ions, which combination with alginate does not form an alginate gel. In certain such embodiments, the concentration of alginate is about 1% (w/w) and the concentration of the metal ions is about 10 mM. In further embodiments, the viscosity of alginate is below about 4 cP at the temperature of about 25° C. in the presence of about 10 mM of said metal ions. In still further embodiments, the alginate gel is not formed within more than about 10 seconds.

In further embodiments, said metal ions crosslink the shell hydrocolloid. The terms "metal ions which crosslink the shell hydrocolloid" or "metal ions which are capable of crosslinking the hydrocolloid present in the shell", as used herein, refer in some embodiments to metal ions, which combination with the shell hydrocolloid forms a hydrocolloid gel. In certain such embodiments, the concentration of the hydrocolloid is about 0.5% (w/w) and the concentration of the metal ions is about 0.25M. In further embodiments, the hydrocolloid gel is formed within less than about 30 seconds.

In some embodiments, the metal ions are magnesium ions. In certain such embodiments, the shell hydrocolloid is gellan.

In some embodiments, the shell hydrocolloid is crosslinked. In further embodiments, the shell hydrocolloid is crosslinked with magnesium ions. In certain such embodiments, the shell hydrocolloid is gellan crosslinked with magnesium ions. The concentration of magnesium ions, which crosslink gellan can range from about 0.075 to about 0.5 mM/g(gellan). In further embodiments, the concentration of magnesium ions, which crosslink gellan ranges from about 0.085 to about 0.4 mM/g(gellan). In certain embodiments, the concentration of magnesium ions, which crosslink gellan ranges from about 0.1 to about 0.25 mM/g (gellan).

It is to be understood that only a fraction of the metal ions, present in the shell, is used to crosslink the shell hydrocolloid. A person skilled in the art would readily realize, however, that the concentration of such "free" metal ions should be kept low, such that they do not interfere with e.g., drug encapsulation or heavy metal ions entrapment.

In some embodiments, the concentration of magnesium ions in the shell, which are not used for crosslinking alginate is lower than about 0.05 mM/g(gellan). In further embodiments, the concentration of said magnesium ions is lower than about 0.04 mM/g(gellan), about 0.03 mM/g(gellan), or about 0.02 mM/g(gellan). Each possibility represents a separate embodiment of the invention.

In some embodiments, the metal ions are potassium ions. In certain such embodiments, the shell hydrocolloid is gellan or k-carrageenan. Each possibility represents a separate embodiment of the invention.

In some embodiments, the shell hydrocolloid is crosslinked. In further embodiments, the shell hydrocolloid is crosslinked with potassium ions. In still further embodiments, the shell hydrocolloid is k-carrageenan crosslinked with potassium ions.

In some embodiments, the weight percent of the potassium ions, which crosslink κ-carrageen ranges from about 0.5% to about 1.5% of the total weight of the shell. In some embodiments, the weight percent of the potassium ions, which crosslink κ-carrageen ranges from about 1% to about 1.3%.

In some embodiments, the shell hydrocolloid is crosslinked. In further embodiments, the shell hydrocolloid is crosslinked with potassium ions. In still further embodiments, the shell hydrocolloid is gellan crosslinked with potassium ions.

In some embodiments, the metal ions are sodium ions. In certain such embodiments, the shell hydrocolloid is gellan. In some embodiments, the shell hydrocolloid is crosslinked. In further embodiments, the shell hydrocolloid is crosslinked with sodium ions. In still further embodiments, the shell hydrocolloid is gellan crosslinked with sodium ions.

In some embodiments, the metal ions are other than calcium ions. In some embodiments, the shell is essentially free of calcium ions. The term "essentially free of calcium ions", as used herein, refers in some embodiments, to a concentration of calcium ions that is lower than about 0.01M. In further embodiments, the concentration of calcium ions in the shell is lower than about 0.005M. In still further embodiments, the concentration of calcium ions in the shell is lower than about 0.00109M.

In some embodiments, the shell further comprises at least one surfactant. The surfactant affords for the thinning of the solid or semi-solid shell, thereby improving heavy metal ion transport into the liquid alginate core. Without wishing to being bound by theory or mechanism of action, it is contemplated that the surfactant decreases the surface tension of the hydrocolloid solution, used in the preparation of the solid or semi-solid shell, thereby providing better "wetting" of the core and leading to thinner shells. A surfactant may comprise a non-ionic, cationic, anionic, amphoteric surfactant or combinations thereof. According to some embodiments, the surfactant is an amphoteric surfactant.

The amphoteric surfactant may include lecithin, N-dodecyl alanine, cocamidopropyl amino betaine or a combination thereof. Each possibility represents a separate embodiment of the invention.

Non-limiting examples of possible non-ionic organic surfactants include polysorbates, such as polyoxyethylene sorbitan monolaurate (Tween 20), polyoxyethylene sorbitan monopalmitate (Tween 40), polyoxyethylene sorbitan monostearate (Tween 60) and polyoxyethylene sorbitan monooleate (Tween 80); glyceryl stearate; polyoxyethylene (POE) fatty acid esters, such as Myrj 45, Myrj 49, Myrj 52 and Myrj 59; sorbitan fatty acid esters, such as sorbitan monolaurate (Span 20), sorbitan monopalmitate (Span 40), sorbitan monooleate (Span 80), sorbitan monostearate (Span 60); mono/diglycerides of octanoic/dectanoic acids, such as but not limited to Imwitor-742, Imwitor-308; poly(oxyethylene) alkylyl ethers, such as poly(oxyethylene) cetyl ether (Brij 52, Brij 56, Brij 58), poly(oxyethylene) palmityl ether, polyethylene oxide hexadecyl ether, polyethylene glycol cetyl ether, and the like; polyethoxylene castor oil derivatives, such as Cremophor EL, ELP and RH 40; PEG-6 octanoic/decanoic glycerides, such as Softigen 767 and the like; polyoxyethylene glycerol trioleate, such as but not limited to Tagat TO; decaglycerol mono/dioleate, such as Caprol PGE860 and the like; sucrose esters of fatty acids, such as but not limited to a sucrose ester of palm oil; and a combination thereof. Each possibility represents a separate embodiment of the invention.

Non-limiting examples of possible cationic surfactants include phosphatides, such as phosphatidyl choline and the like; quaternary ammonium cationic surfactants, such as hexadecyltrimethyl ammonium bromide and the like; pyrimidinium cationic surfactants, such as, but not limited to dodecyl pyridinium chloride; and a combination thereof.

The anionic surfactants useful in the preparation of the capsules of the present invention include sodium alkyl sulfates, such as, but not limited to sodium lauryl sulfate; sodium alkyl sulfonates; sodium alkyl aryl sulfonates, such as sodium dodecyl benzene sulfonate and the like; sodium stearate; dioctyl sodium sulfosuccinate; sodium cholate; and combinations thereof. Each possibility represents a separate embodiment of the invention.

In certain embodiments, the surfactant is selected from the group consisting of lecithin; sultaines CHAPS (3-[(3-Cholamidopropyl)dimethylammonio]-1-propanesulfonate); cocamidopropyl hydroxysultaine; cocamidopropyl betaine; phosphatidylserine; phosphatidylethanolamine; phosphatidylcholine; sphingomyelin and combinations thereof. Each possibility represents a separate embodiment of the invention. In some exemplary embodiments, the surfactant comprises lecithin.

The type and the amount of surfactant may be determined by a person skilled in art so as to obtain the desired thinning of the capsule shell. In some exemplary embodiments, the surfactant is lecithin.

In some embodiments, the surfactant is present in the shell in a concentration ranging from about 5 ppm to about 500 ppm. In certain embodiments, the concentration of the surfactant in the shell is from about 5 ppm to about 400 ppm, from about 5 ppm to about 300 ppm, from about 5 ppm to about 200 ppm, from about 5 ppm to about 100 ppm, or from about 5 ppm to about 50 ppm. Each possibility represents a separate embodiment of the invention.

The shell can further include an additional polymer. Without wishing to being bound by theory or mechanism of action, the additional polymer affords for the mechanical strengthening of the solid or semi-solid shell. In some embodiments, said polymer is an additional hydrocolloid. In some embodiments, said polymer is a polycation. Without further wishing to being bound by theory or mechanism of action, it is contemplated that when the pKa of the polymer is lower than the surrounding pH, a polycations-polyanion interaction can occur between the negative charge of the shell hydrocolloid and the positive charge of the polycation functional groups. Said interactions can strengthen the shell of the capsule. In some embodiments, the polycation has a positively charged amine group. The non-limiting examples of the suitable polycations include poly-L-lysine (PLL), polyarginine, chitosan, and combinations thereof.

In some embodiments, the polycation has a molecular weight of less than about 100 kDa. In further embodiments, the polycation has a molecular weight of less than about 75 kDa. In yet further embodiments, the polycation has a molecular weight of less than about 50 kDa. In still further embodiments, the polycation has a molecular weight of less than about 40 kDa. In yet further embodiments, the polycation has a molecular weight of less than about 20 kDa.

In some embodiments, the capsule is essentially spherical. In some embodiments, the term "essentially spherical" refers to a capsule having an aspect ratio of from about 0.90 to about 1.

The aspect ratio can be calculated according to the following formula, $$\text{Aspect ratio} = \frac{D_{max}}{D_{min}} \quad \text{Formula (2)}$$

wherein $D_{max}$ is the largest length of the capsule in the first dimension and $D_{min}$ is the smallest length of the capsule in the second dimension. In some embodiments, the first dimension is perpendicular to the second dimension.

In further embodiments, the aspect ratio of the capsule is at least about 0.90, at least about 0.91, at least about 0.92, at least about 0.93, at least about 0.94, or at least about 0.95. Each possibility represents a separate embodiment of the invention.

The Feret diameter of the capsule along the longest dimension thereof can range from about 50 μm to about 10 cm. In further embodiments, the Feret diameter of the capsule ranges from about 50 μm to about 5 cm, from about 50 μm to about 1 cm, from about 100 μm to about 1 cm, from about 200 μm to about 1 cm, from about 100 μm to about 0.5 cm, or from about 200 μm to about 1 cm. Each possibility represents a separate embodiment of the invention.

In some embodiments, the capsule is essentially spherical. In certain such embodiments, the diameter of the capsule ranges from about 50 μm to about 10 cm. In further embodiments, the diameter of the capsule ranges from about 50 μm to about 5 cm, from about 50 μm to about 1 cm, from about 100 μm to about 1 cm, from about 200 μm to about 1 cm, from about 100 μm to about 0.5 cm, or from about 200 μm to about 1 cm. Each possibility represents a separate embodiment of the invention.

In some embodiments, the volume of the alginate solution ranges from about 50 μL to about 1 ml. In further embodiments, the volume of the alginate solution ranges from about 100 μL to about 1 ml. In still further embodiments, the volume of the alginate solution ranges from about 200 μL to about 900 μL, from about 300 μL to about 800 μL, or from about 400 μL to about 700 μL. Each possibility represents a separate embodiment of the invention.

In some embodiments, the diameter of the liquid alginate core ranges from about 1 to about 10 mm. In further embodiments, the diameter of the liquid alginate core ranges from about 1 to about 7 mm. In still further embodiments, the diameter of the liquid alginate core ranges from about 2 to about 6 mm. In yet further embodiments, the diameter of the liquid alginate core ranges from about 3 to about 5 mm. In certain embodiments, the diameter of the liquid alginate core is about 4 mm.

In some embodiments, the shell thickness ranges from about 0.1 mm to about 1.3 mm. In further embodiments, the shell thickness ranges from about 0.2 mm to about 1.2 mm. In still further embodiments, the shell thickness ranges from about 0.3 mm to about 1.1 mm. In yet further embodiments, the shell thickness ranges from about 0.4 mm to about 1.0 mm.

The volume (v/v) ratio between the liquid alginate core and the shell can range from about 0.2:1 to about 1.5:1. In some embodiments, the volume (v/v) ratio between the liquid alginate core and the shell ranges from about 0.4:1 (for relatively thick shells, e.g., for a shell having a thickness of about 970 μm) to about 1.25:1 (for relatively thin shells, e.g., for a shell having a thickness of about 420 μm). In further embodiments, the volume ratio between the liquid alginate core and the shell ranges from about 0.5:1 to about 1.2:1, from about 0.6:1 to about 1.1:1, or from about 0.7:1 to about 1:1.

A person skilled in the art will readily realize that the weight of the hydrocolloid-based capsule of the present invention can vary significantly, depending on the type of the shell polymer, the thickness of the shell and the presence and amount of the surfactant and the additional polymer in the shell. In some exemplary embodiments, the weight of the capsule ranges from about 100 to about 200 mg.

The hydrocolloid-based liquid-core capsules according to the principles of the present invention are characterized by very good mechanical properties. In some embodiments, the capsule has a stress at failure ranging from about 5 kPa to about 50 kPa. In some embodiments, the capsule has a stress at failure ranging from about 10 kPa to about 40 kPa. In certain embodiments, the capsule has a stress at failure of at least about 5 kPa. In further embodiments, the capsule has a stress at failure of at least about 10 kPa, at least about 15 kPa, at least about 20 kPa, or at least about 25 kPa. Each possibility represents a separate embodiment of the invention.

In some embodiments, the capsule has a strain at failure ranging from about 0.35 to about 0.75. In further embodiments, the capsule has a strain at failure ranging from about 0.45 to about 0.65. In some embodiments, the capsule has a strain at failure of at least about 0.35. In some embodiments, the capsule has a strain at failure of at least about 0.40, of at least about 0.45, of at least about 0.5, or of at least about 0.55. Each possibility represents a separate embodiment of the invention.

The hydrocolloid-based liquid-core capsules according to the principles of the present invention are characterized by very high adsorption capacity of heavy metal ions. The non-limiting examples of heavy metal ions that can be adsorbed by the capsules of the present invention include chromium, cobalt, nickel, copper, zinc, arsenic, selenium, silver, cadmium, antimony, mercury, thallium, lead ion and combinations thereof.

In some embodiments, the capsule is characterized by an adsorption capacity of lead cations of at least about 150 mg(lead)/g(alginate). In further embodiments, the capsule is characterized by an adsorption capacity of lead cations of at least about 160 mg(lead)/g(alginate), at least about 170 mg(lead)/g(alginate), at least about 180 mg(lead)/g(alginate), at least about 190 mg(lead)/g(alginate), at least about 200 mg(lead)/g(alginate), at least about 210 mg(lead)/g(alginate), at least about 220 mg(lead)/g(alginate), at least about 230 mg(lead)/g(alginate), at least about 240 mg(lead)/g(alginate), at least about 250 mg(lead)/g(alginate), or even at least about 260 mg(lead)/g(alginate). Each possibility represents a separate embodiment of the invention. In certain embodiments, the capsule is characterized by an adsorption capacity of lead cations of about 267 mg(lead)/g(alginate).

In some embodiments, the capsule is characterized by an adsorption capacity of copper cations of at least about 150 mg(copper)/g(alginate). In further embodiments, the capsule is characterized by an adsorption capacity of copper cations of at least about 160 mg(copper)/g(alginate), at least about 170 mg(copper)/g(alginate), at least about 180 mg(copper)/g(alginate), at least about 190 mg(copper)/g(alginate), at least about 200 mg(copper)/g(alginate), or even at least about 210 mg(copper)/g(alginate). Each possibility represents a separate embodiment of the invention. In certain embodiments, the capsule is characterized by an adsorption capacity of copper cations of about 219 mg(copper)/g(alginate).

In some embodiments, the capsule is characterized by an adsorption capacity of cadmium cations of at least about 130 mg(cadmium)/g(alginate). In further embodiments, the capsule is characterized by an adsorption capacity of cadmium cations of at least about 140 mg(cadmium)/g(alginate), at least about 150 mg(cadmium)/g(alginate), at least about 160 mg(cadmium)/g(alginate), at least about 170 mg(cadmium)/g(alginate), at least about 180 mg(cadmium)/g(alginate), or even at least about 190 mg(cadmium)/g(alginate). Each possibility represents a separate embodiment of the invention. In certain embodiments, the capsule is characterized by an adsorption capacity of cadmium cations of about 197 mg(cadmium)/g(alginate).

In some embodiments, the capsule is characterized by an adsorption capacity of nickel cations of at least about 50 mg(nickel)/g(alginate). In certain embodiments, the capsule is characterized by an adsorption capacity of nickel cations of about 65 mg(nickel)/g(alginate).

One of the additional beneficial features of the disclosed capsules is that said capsules retain the mechanical strength thereof even following adsorption of the heavy metal ions. In has been surprisingly found that the stress value at failure was increased by more than 100% following heavy metal adsorption. It has further been found that the capsule retained 100% of the strain value at failure following adsorption of the heavy metal ions. Accordingly, in some embodiments, the stress and strain values at failure do not change or are improved following the adsorption of heavy metal ions. Each possibility represents a separate embodiment of the invention.

In another aspect there is provided a method for the preparation of the hydrocolloid core-shell capsule of the invention, the method comprising: (i) preparing a mixture of alginate ions and metal ions, which do not crosslink alginate and are capable of crosslinking the shell hydrocolloid; (ii) providing a hydrocolloid solution, wherein the hydrocolloid is other than alginate; (iii) dripping the mixture of alginate ions and metal ions into the hydrocolloid solution under constant mixing; and (iv) suspending the mixture formed in step (iii), thereby forming the hydrocolloid core-shell capsules. The metal ion can be selected from magnesium ions, potassium ions and sodium ions. Each possibility represents a separate embodiment of the invention. In some exemplary embodiments, said metal ions are magnesium ions.

In another aspect, there is provided a method for the preparation of the capsules of the invention, the method comprising: (1) preparing a magnesium-alginate mixture; (2) providing a hydrocolloid solution; (3) dropping the magnesium alginate mixture into the hydrocolloid solution at a predefined rate and under constant mixing; (4) suspending the mixture formed in step (3) for a predefined time, thereby forming alginate liquid core, hydrocolloid polymer shell capsules; (5) washing the capsules obtained in step (4).

The process is preferably a one-step process. The term "one-step" process, as used herein, refers in some embodiments to the process, wherein the liquid alginate core is formed in one step. In further embodiments, the term refers to a process, which does not require conversion of a solid alginate core to a liquid alginate core.

According to some embodiments, the step of preparing a mixture of alginate ions and metal ions comprises mixing a solution of alginate salt or alginic acid ester and a solution of metal salt. The non-limiting examples of alginate salts include sodium, potassium, and ammonium salts. In some embodiments, the alginate salt is present in the mixture in a weight percent of from about 0.5% to about 10% of the total weight of the mixture. In further embodiments, the alginate salt is present in the mixture in a weight percent of from about 0.75% to about 7.5% of the total weight of the mixture. In still further embodiments, the alginate salt is present in the mixture in a weight percent of from about 1% to about 5% of the total weight of the mixture. In yet further embodiments, the alginate salt is present in the mixture in a weight percent of from about 2% to about 4% of the total weight of the mixture.

The alginic acid ester can be PGA. In some embodiments, the alginic acid ester is present in the mixture in a weight percent of from about 0.5% to about 10% of the total weight of the mixture. In further embodiments, PGA is present in the mixture in a weight percent of from about 0.75% to about 7.5% of the total weight of the mixture. In still further embodiments, PGA is present in the mixture in a weight percent of from about 1% to about 5% of the total weight of the mixture. In yet further embodiments, PGA is present in the mixture in a weight percent of from about 2% to about 4% of the total weight of the mixture.

The non-limiting examples of the metal salts include magnesium chloride, magnesium oxide, magnesium citrate, magnesium orotate, magnesium lactate, magnesium sulfate, magnesium carbonate, potassium chloride, potassium carbonate, and combinations thereof.

In certain embodiments, the metal salt is magnesium chloride. In some embodiments, the magnesium salt is present in the mixture in the molar concentration of from about 0.25M to about 1.5M. In further embodiments, the magnesium salt is present in the mixture in the molar concentration of from about 0.25M to about 1M. In further embodiments, the magnesium salt is present in the mixture in the molar concentration of from about 0.3M to about 0.7M. The inventors of the present invention have unexpectedly discovered that the magnesium salt solution concentrations lower than the above range led to the formation of the capsules which were not essentially spherical and had a poor mechanical strength. Magnesium salt solution concentrations being substantially higher than said range could result in the excess of magnesium ions in the shell, thereby interfering with adsorption of additional cations into the capsule.

In some exemplary embodiments, the magnesium-alginate mixture is formed by dissolving sodium-alginate in a magnesium salt solution. In further experimental embodiments, sodium alginate is present in the magnesium-alginate mixture in a weight percent of about 3% w/w. In yet further experimental embodiments, the molecular weight of sodium alginate is about 60-70 kDa. In still further experimental embodiments, the concentration of the $MgCl_2$ solution is about 0.5 M.

In some embodiments, the mixture of the metal ions and alginate ions has a temperature of from about 20° C. to about 30° C. In further embodiments, the magnesium-alginate mixture has a temperature of from about 20° C. to about 30° C. Inventors of the present invention have surprisingly found that the mixture temperatures lower than said range did not allow formation of essentially spherical capsules. The inventors have further found that the drops of the magnesium-alginate mixture having temperature higher than said range did not penetrate the hydrocolloid solution. In certain embodiments, the mixture of the metal ions and alginate ions has a temperature of about 25° C. In further embodiments, the magnesium-alginate mixture has a temperature of about 25° C.

The non-limiting examples of suitable hydrocolloids include gellan and k-carrageenan. The hydrocolloid can be present in the hydrocolloid solution in a weight percent of from about 0.1% to about 1.5% of the total weight of the solution. In some embodiments, the hydrocolloid is present in the hydrocolloid solution in a weight percent of from about 0.2% to about 1% of the total weight of the solution. In further embodiments, the hydrocolloid is present in the hydrocolloid solution in a weight percent of from about 0.25% to about 0.95% of the total weight of the solution. In still further embodiments, the hydrocolloid is present in the hydrocolloid solution in a weight percent of from about 0.25% to about 0.75% of the total weight of the solution.

In some exemplary embodiments, the hydrocolloid solution is provided by dissolving gellan in distilled water and heating the solution until complete dissolution of gellan. The solution can be heated to about 60° C.-100° C. In further exemplary embodiments, gellan is a low acyl gellan gum. In certain embodiments, gellan is present in the hydrocolloid solution in a weight percent of from about 0.25% to about 0.95% of the total weight of the solution. The inventors of the present invention have unexpectedly discovered that at the hydrocolloid solution concentrations lower than the above range an essentially spherical capsule could not be formed and at the concentrations lower than said range magnesium-alginate drops could not penetrate the hydrocolloid solution.

In some embodiments, the hydrocolloid solution is cooled down prior to step (iii) or (3) (i.e. the dripping step). In some embodiments, the hydrocolloid solution has a temperature of from about 25° C. to about 35° C. during the dripping step. The inventors have further found that at the mixture temperatures higher than said range capsules were not formed and at the lower temperatures, gelation of the gellan solution was observed. In certain embodiments, the mixture of the hydrocolloid solution has a temperature of about 30° C. In further embodiments, the gellan solution has a temperature of about 30° C.

In some embodiments, the mixture of alginate ions and metal ions has a higher density and/or viscosity than the hydrocolloid solution. Each possibility represents a separate embodiment of the invention.

In some embodiments, the density of the mixture of alginate ions and metal ions ranges from about 1 $g/cm^3$ to about 1.2 $g/cm^3$. In further embodiments, the density of the mixture of alginate ions and metal ions ranges from about 1.05 $g/cm^3$ to about 1.16 $g/cm^3$. In certain embodiments, the density of said mixture is about 1.1 $g/cm^3$.

In some embodiments, the density of the hydrocolloid solution ranges from about 0.9 $g/cm^3$ to about 1.1 $g/cm^3$. In further embodiments, the density of the hydrocolloid solution ranges from about 0.96 $g/cm^3$ to about 1.04 $g/cm^3$. In certain embodiments, the density of the hydrocolloid solution is about 1 $g/cm^3$.

In some embodiments, the viscosity of the mixture of alginate ions and metal ions ranges from about 200 to about 1200 cP at 6.5 l/sec shear rate and temperature of about 25° C. In further embodiments, the viscosity of the mixture of alginate ions and metal ions ranges from about 500 to about 1000 cP at 6.5 l/sec shear rate and temperature of about 25° C. In still further embodiments, the viscosity of said mixture ranges from about 600 to about 800 cP at 6.5 l/sec shear rate and temperature of about 25° C. In certain embodiments, the viscosity of the mixture of alginate ions and metal ions is about 700 cP at 6.5 l/sec shear rate and temperature of about 25° C.

In some embodiments, the viscosity of the hydrocolloid solution ranges from about 1 to about 100 cP at 6.5 l/sec shear rate and temperature of about 30° C. In further embodiments, the viscosity of the hydrocolloid solution ranges from about 1 to about 50 cP at 6.5 l/sec shear rate and temperature of about 30° C. In still further embodiments, the viscosity of the hydrocolloid solution ranges from about 1 to about 20 cP at 6.5 l/sec shear rate and temperature of about 30° C. In yet further embodiments, the viscosity of the hydrocolloid solution ranges from about 5 to about 15 cP at 6.5 l/sec shear rate and temperature of about 30° C. In certain embodiments, the viscosity of the hydrocolloid solution is about 9 cP at 6.5 l/sec shear rate and temperature of about 30° C.

In some embodiments, the surface tension of the mixture of alginate ions and metal ions ranges from about 20 to about 60 mN/m. In further embodiments, the surface tension of the mixture of alginate ions and metal ions ranges from about 35 to about 50 mN/m. In certain embodiments, the surface tension of said mixture is about 43 mN/m.

In some embodiments, the surface tension of the hydrocolloid solution ranges from about 50 to about 90 mN/m. In further embodiments, the surface tension of the hydrocolloid solution ranges from about 60 to about 80 mN/m. In still further embodiments, the surface tension of the hydrocolloid solution ranges from about 65 to about 75 mN/m. In certain embodiments, the surface tension of the hydrocolloid solution is about 71 mN/m.

In some embodiments, the density of the mixture of magnesium and alginate ions ranges from about 1 $g/cm^3$ to about 1.2 $g/cm^3$. In further embodiments, the density of the mixture of magnesium and alginate ions ranges from about 1.05 $g/cm^3$ to about 1.16 $g/cm^3$. In certain embodiments, the density of the mixture of magnesium and alginate ions is about 1.1 $g/cm^3$.

In some embodiments, the density of the gellan solution ranges from about 0.9 $g/cm^3$ to about 1.1 $g/cm^3$. In further embodiments, the density of the gellan solution ranges from about 0.96 $g/cm^3$ to about 1.04 $g/cm^3$. In certain embodiments, the density of the gellan solution is about 1 $g/cm^3$.

In some embodiments, the viscosity of the mixture of magnesium and alginate ions ranges from about 200 to about 1200 cP at 6.5 l/sec shear rate and temperature of about 25° C. In further embodiments, the viscosity of the mixture of magnesium and alginate ions ranges from about 500 to about 1000 cP at the temperature of about 25° C. In still further embodiments, the viscosity of the mixture of magnesium and alginate ions ranges from about 600 to about 800 cP at 6.5 l/sec shear rate and temperature of about 25° C. In certain embodiments, the viscosity of the mixture of magnesium and alginate ions is about 700 cP at 6.5 l/sec shear rate and temperature of about 25° C.

In some embodiments, the viscosity of the gellan solution ranges from about 1 to about 100 cP at 6.5 l/sec shear rate and temperature of about 30° C. In further embodiments, the viscosity of the gellan solution ranges from about 1 to about 50 cP at 6.5 l/sec shear rate and temperature of about 30° C. In still further embodiments, the viscosity of the gellan solution ranges from about 1 to about 20 cP at 6.5 l/sec shear rate and temperature of about 30° C. In yet further embodiments, the viscosity of the gellan solution ranges from about 5 to about 15 cP at 6.5 l/sec shear rate and temperature of about 30° C. In certain embodiments, the viscosity of the gellan solution is about 9 cP at 6.5 l/sec shear rate and temperature of about 30° C.

In some embodiments, the surface tension of the mixture of magnesium and alginate ions ranges from about 20 to about 60 mN/m. In further embodiments, the surface tension of the mixture of magnesium and alginate ions ranges from about 35 to about 50 mN/m. In certain embodiments, the surface tension of the mixture of magnesium and alginate ions is about 43 mN/m.

In some embodiments, the surface tension of the gellan solution ranges from about 50 to about 90 mN/m. In further embodiments, the surface tension of the gellan solution ranges from about 60 to about 80 mN/m. In still further embodiments, the surface tension of the gellan solution ranges from about 65 to about 75 mN/m. In certain embodiments, the surface tension of the gellan solution is about 71 mN/m.

In some embodiments, the dripping of the mixture of the metal ions and alginate ions is performed at a rate ranging from about 0.25 ml/sec to about 30 ml/sec. In further embodiments, the dripping is performed at a rate of from about 0.5 ml/sec to about 20 ml/sec. In yet further embodiments, the dripping is performed at a rate of from about 0.75 ml/sec to about 10 ml/sec. In still further embodiments, the dripping is performed at a rate of from about 1 ml/sec to about 5 ml/sec. In certain embodiments, the dripping is performed at a rate of about 3 drops per second. The terms "dripping" and "dropping" are used herein interchangeably.

The dripping of the mixture of the metal ions and alginate ions can be performed from a height of about 1 to about 5 cm above the surface of the hydrocolloid solution. In some embodiments, said height is about 2.5 cm.

The constant mixing can be performed at a rate of from about 20 rpm to about 500 rpm. In some embodiments, the mixing is performed at a rate of from about 100 rpm to about 500 rpm. In certain embodiments, the constant mixing is performed at 300 rpm. The mixing can be carried out by any suitable technique, known in the art.

The mixture formed in step (iii) or (3) can be suspended in step (iv) or (4) for a period of 0.1 minutes to about 10 minutes. In some embodiments, the mixture is suspended for 0.1 to 5 minutes or from about 0.5 to 2 minutes. Each possibility represents a separate embodiment of the invention.

In some embodiments, the method comprises the step of washing the obtained capsules. Preferably the washing is done in distilled water for at least about 2 times. In certain embodiments, the washing is performed for 2-5 times. In some exemplary embodiments, the capsules are washed for three times.

According to some embodiments, the hydrocolloid solution comprises a surfactant. In certain embodiments, the surfactant is selected from the group consisting of lecithin; sultaines CHAPS (3-[(3-Cholamidopropyl)dimethylammonio]-1-propanesulfonate); cocamidopropyl hydroxysultaine; cocamidopropyl betaine; phosphatidylserine; phosphatidylethanolamine; phosphatidylcholine; sphingomyelin and combinations thereof. Each possibility represents a separate embodiment of the invention. In some exemplary embodiments, the surfactant comprises lecithin.

The concentration of the surfactant can range from about 5 ppm to about 500 ppm. In some embodiments, the concentration of the surfactant is from about 5 ppm to about 400 ppm, from about 5 ppm to about 300 ppm, from about 5 ppm to about 200 ppm, from about 5 ppm to about 100 ppm, or from about 5 ppm to about 50 ppm. Each possibility represents a separate embodiment of the invention. In some exemplary embodiments, the concentration of the surfactant is 20 ppm.

In some embodiments, the method comprises an additional step comprising contacting the capsules with a crosslinking agent or with a polycation. Each possibility represents a separate embodiment of the invention. Said contacting can be performed by any method known in the art, such as, but not limited to, immersing the capsules in a solution comprising a crosslinking agent or a polycation or applying said solution to the capsules. Said contacting can be performed for a period of from about 5 minutes to about 60 minutes. In certain embodiments, said contacting is performed for a period of from about 10 minutes to about 40 minutes. In some exemplary embodiments, the capsules are immersed in the solution comprising a crosslinking agent or a polycation for about 20 minutes.

In certain embodiments, the crosslinking agent comprises magnesium ions. In further embodiments, the crosslinking agent comprises a solution of magnesium salt, such as, but not limited to, magnesium chloride. In some embodiments, the solution of magnesium salt has a molar concentration of from about 0.1M to about 1.5M. In further embodiments, the solution of magnesium salt has a molar concentration of from about 0.2M to about 1M. In yet further embodiments, the molar concentration ranges from about 0.3M to about 0.7M. In some exemplary embodiments, the molar concentration of magnesium chloride is about 0.5M.

The polycation can be a polymer having a positively charged amino group. The non-limiting examples of suitable polycations include poly-L-lysine, polyarginine, chitosan, and combinations thereof.

The capsules according to the principles of the present invention are suitable for use in various technological applications, including, but not limited to, water treatment, food industry, agriculture, pharmacology, biotechnology, medicinal technologies and environmental applications. For example, the capsules can be used for pesticide, drug or cell encapsulation, or in medical devices.

In certain embodiments, the capsules are for use in the removal of heavy metal ions. It has been found by the inventors of the present invention that the liquid alginate core has heavy-metal ion adsorption efficiency, which is higher than of the currently known solid alginate-based capsules. The mechanical strength and the reusability of the capsules provide further benefits for the utilization thereof in the water treatment technology.

Accordingly, in another aspect there is provided a device comprising a plurality of capsules according to the principles of the present invention. In some embodiments, the plurality of capsules is immobilized within said device, said immobilization enabling flow of a liquid through the device.

The term "immobilized" refers to capsules that have been arranged in such a manner so they will not move when the liquid containing the heavy metal ions, comes into contact with the capsules.

The device can further comprise a container, wherein the container comprises a sieve. In further embodiments, the container comprises an inlet and an outlet, suitable for passing the liquid therethrough. In some embodiments, the sieve has pores which are smaller than the size of the capsules. In further embodiments, the sieve has pores smaller than about 100 µm.

Immobilization of the capsules can be done, for example, by constructing a device being a container having a sieve dividing the container into two parts, a first part comprising the capsules and a second part devoid of the capsules. The liquid to be treated flows through the first part, coming into contact with the capsules, and then flows to the second part, while the capsules due to their size are retained in the first part of the container by the sieve. The container may have an inlet in the first part for entrance of the liquid to be treated and an outlet in the second part for the exit of the treated liquid.

Another alternative structure of the device is a filtering column in which the capsules are retained/packed. Flow modifiers (for example, prepared from plastic) can be introduced among the capsules to facilitate free flow of aqueous liquid containing the heavy metal ions.

In another aspect there is provided a method of removal of heavy metal ions from a liquid-containing environment, the method comprising bringing the capsules or the device according to the principles of the present invention in contact with the liquid-containing environment, for a time and under conditions enabling entry and entrapment of the heavy metal ion into the capsules.

In some embodiments, the liquid-containing environment is a liquid. In some embodiments, the liquid-containing environment is a gel or a gel-like material. In some embodiments, the liquid-containing environment is a solid comprising moisture. In further embodiments, the solid comprises at least about 20% moisture. In still further embodiments, the solid comprises at least about 30% moisture. In some embodiments, the liquid-containing environment is a gas comprising moisture. The moisture can be present in the gas in the form of water droplets.

In some embodiments, the liquid is an aqueous liquid. In further embodiments, the liquid is water. In some embodiments, the liquid comprises an emulsion. Said emulsion can include water and oil in different proportions.

The term "heavy-metal", as used herein, refers in some embodiments, to metals having a density of greater than 5 g/cm$^3$. The non-limiting examples of heavy-metal ions, which can be removed by the capsules or device of the present invention include chromium, cobalt, nickel, copper, zinc, arsenic, selenium, silver, cadmium, antimony, mercury, thallium and lead. In some currently preferred embodiments, the heavy-metal ions include lead, copper, cadmium, nickel and combinations thereof.

In some embodiments, the pH of the liquid-containing environment containing heavy metal ions is adjusted to about 4-7. In certain embodiments, the pH is about 5-6. In some exemplary embodiments, the pH is about 5.5. Without wishing to being bound by theory or mechanism of action, it is contemplated that lower pH values of the liquid-containing environment containing the heavy-metal ions reduce the adsorption efficiency of the capsules due to the interaction of the carboxyl groups of the shell hydrocolloid and protons. At higher pH values, metal ions tend to precipitate as hydroxyl salts.

The time of contact between the capsules and the liquid-containing environment can be from about 30 minutes to about 500 minutes. In some embodiments, the time of contact is from about 30 minutes to about 60 minutes. In other embodiments, the time of contact is 60-500 minutes, such as, 60-480 minutes, 60-360 minutes, 60-240 minutes, or 60-120 minutes. Each possibility represents a separate embodiment of the invention.

In some embodiments, the capsules are immobilized. In further embodiments, the method comprises the step of separation been the immobilized capsules and the treated liquid. The treated liquid can be separated from the capsules, for example, by flowing the liquid through a sieve on which the capsules are retained due to their size, or through column in which the capsules are packed. The step of bringing the liquid into contact with the capsules or the device can be repeated following the separation between the capsules and the liquid. In some embodiments, said step is repeated at least twice. In further embodiments, said step is repeated for at least three times.

In some embodiments, the method comprises regeneration of the capsules. The term "regeneration", as used herein, refers to extracting the heavy metal ions entrapped in the capsules, rendering them suitable for further use. Regeneration of the capsules can be performed by suspending the capsules in an acid. The acid can be any strong acid, which does not decompose the capsule. The non-limiting examples of suitable acids include $HNO_3$, $H_2SO_4$, HCl, HI, HBr, $HClO_4$, and combinations thereof. The concentration of the acid can range from about 0.5M to about 3M. In some embodiments, the concentration of the acid ranges from about 0.5M to about 2M. In some exemplary embodiments, the concentration of the acid is about 1M.

In some embodiments, the capsules are suspended in the acid for from about 6 to about 54 hours. In further embodiments, the capsules are suspended in the acid for from about 12 to about 48 hours. In some exemplary embodiments, the capsules are suspended for about 24 hours.

The regeneration procedure can further include a step of washing of the capsules until a neutral pH is reached. In some embodiments, the regeneration procedure further includes an additional step comprising contacting the capsules with a crosslinking agent. Said contacting can be performed for from about 5 minutes to about 60 minutes. In certain embodiments, the crosslinking agent comprises magnesium ions. In further embodiments, the crosslinking agent comprises a solution of magnesium salt, such as, but not limited to, magnesium chloride. In certain embodiments, the solution of magnesium salt has a molar concentration of from about 0.1M to about 1.5M. In further embodiments, the solution of magnesium salt has a molar concentration of from about 0.2M to about 1M. In yet further embodiments, the molar concentration ranges from about 0.3M to about 0.7M. In some exemplary embodiments, the molar concentration of magnesium chloride is about 0.5M.

In some embodiments, the method includes multiple regeneration procedures of the capsules. In some embodiments, the method includes at least two regeneration processes. In further embodiments, the method includes at least three regeneration processes.

In certain embodiments, the method includes 1-3 regeneration procedures of the capsules.

In some embodiments, the capsules retain at least about 80% of the initial heavy metal ion adsorption capacity thereof following regeneration. In further embodiments, the capsules retain at least about 50% of the initial heavy metal ion adsorption capacity thereof following multiple regenerations.

In some embodiments, the capsules retain at least about 60% of the stress value at failure following regeneration. In further embodiments, the capsules retain at least about 90% of the strain value at failure following regeneration.

As used herein and in the appended claims the singular forms "a", "an," and "the" include plural references unless the content clearly dictates otherwise. Thus, for example, reference to "capsule" includes a plurality of such capsules and equivalents thereof known to those skilled in the art, and so forth. It should be noted that the term "and" or the term "or" is generally employed in its sense including "and/or" unless the content clearly dictates otherwise.

As used herein, the term "about", when referring to a measurable value such as an amount, a temporal duration, and the like, is meant to encompass variations of +/−20%, more preferably +/−5%, even more preferably +/−1%, and still more preferably +/−0.1% from the specified value, as such variations are appropriate to perform the disclosed methods.

The terms "plurality" or "multiple", as used herein, means two or more.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1—Materials and Methods

Preparation of Gellan-Alginate Liquid-Core Capsules

Sodium-alginate (3% w/w, 60-70 kDa, M:G 61:39, Sigma, Chemical Co., St. Louis, Mo., USA) was dissolved in 0.5 M $MgCl_2$ (Sigma-Aldrich Co., Steinheim, Germany) using a magnetic stirrer (model F-13, Freed Electric, Haifa, Israel). Low-acyl gellan gum (0.5% w/w, CP Kelco, Atlanta, Ga., USA) was dissolved in distilled water and heated to 80° C. for complete dissolution. The solution was then cooled to 30° C. Gellan-alginate liquid-core capsules were prepared in single-step process described for water or sucrose liquid core capsules [Nussinovitch et al., Food Hydrocolloids, 11 pp. 209-215, 1997] by dropping the magnesium-alginate mixture at a rate of 3 drops per second into the continuously stirred (300 rpm) gellan solution. The drops were suspended in the gellan solution for various times (0.5, 1.0, 1.5, 2.0 min), until the gellan-magnesium membrane, entrapping alginate fluid within the capsule, formed. The liquid-core capsules were washed three times with distilled water before use in the experiments. For membrane strengthening, the capsules were immersed for 20 min in one of three different solutions: poly-L-lysine (PLL) [B. Thu, P. Bruheim, T. Espevik, O. Smidsrød, P. Soon-Shiong, G. Skjåk-Bræk, Alginate polycation microcapsules: II. Some functional properties, Biomaterials 17 (1996) 1069-1079] (Sigma), chitosan (Sigma) [A. Nussinovitch, Z. Gershon, M. Nussinovitch, Liquid-core hydrocolloid capsules, Food Hydrocolloids 10 (1996) 21-26] or 0.5 M $MgCl_2$ (Sigma-Aldrich). Membrane thinning was achieved by adding 20 ppm surface-active lecithin (Lucas Meyer GmbH, Hamburg, Germany) to the gellan solution during the capsule-production step (Bremond et al., 2010). Surface tension of the gellan solution was measured with a Delta-Pi microtensiometer (Kibron Inc., Helsinki, Finland).

Characterization of the Alginate-Gellan Liquid-Core Capsules

The alginate-gellan liquid-core capsules were digitally imaged under a binocular (model 5ZX16, Olympus America Inc., Center Valley, Pa., USA) and their physical properties (diameter, membrane thickness and inside diameter) were measured using the image analysis software Image J (model 1.48 d, NIH, Bethesda, Md., USA) [R. Lagoa, J. Rodrigues, Evaluation of dry protonated calcium alginate beads for biosorption applications and studies of lead uptake, Appl. Biochem. Biotechnol. 143 (2007) 115-128].

The aspect ratio of the capsule, i.e. its roundness, was calculating by Formula 2, hereinabove.

Values closer to 1 indicated rounder beads (a value of 1 indicating a perfect sphere). Seven specimens from two different batches of each capsule type were examined.

Metal-Adsorption Evaluation

The metal salts $Pb(NO_3)_2$, $CuCl_2 \cdot 2H_2O$, $3CdSO_4 \cdot 8H_2O$, $CdSO_4 \cdot H_2O$, all from Merck KGaA (Darmstadt, Germany), were dissolved in distilled water using a magnetic stirrer to obtain 1,100-1,200 ppm solutions. The pH of the metal solutions was adjusted by titration with 0.1 M NaOH (Frutarom Ltd., Haifa, Israel) or 0.1 M nitric acid ($HNO_3$) (Merck KGaA) and the pH was measured using a pH meter (model C830, Consort, Turnhout, Belgium). Gellan-alginate capsules (containing 0.3 g dry alginate) were added to 0.1 L of each metal solution and stirred using a magnetic stirrer for 8 h at 25° C. to achieve equilibration. The concentration of the cation solutions was measured by ICP-AES (Spectroflame ICP, Spectro Analytical Instruments, Bosch-Str., Germany). Adsorption capacity (mg cation/g dry alginate) was calculated as the difference in cation concentration in the pre- and post-adsorption solutions divided by the weight of the dry alginate [Lagoa and Rodrigues, 2007]:

$$q = \frac{(C_0 - C_e) \cdot V}{W} \qquad (2)$$

where $C_0$ is the initial cation concentration (ppm), $C_e$ is the final cation concentration (ppm), V is the volume of the cation solution (L), and W is the weight of the dry alginate (g). Presented results are averages of four different experiments.

Mechanical Properties of the Capsules

The mechanical properties of the gellan-alginate liquid-core capsules were determined by compression using an Instron Universal Testing Machine (UTM) (model 554, Instron Corporation, Canon, Mass., USA). A special program (Merlin) enabled data conversion of the Instron's voltage versus time measurements into digitized force-deformation values. The force and deformation data were converted to stress versus engineering strain [A. Nussinovitch, Z. Gershon, M. Nussinovitch, Temperature stable liquid core hydrocolloid capsules, Food Hydrocolloids 11 (1997) 209-215, A. Nussinovitch, Z. Gershon, M. Nussinovitch, Liquid-core hydrocolloid capsules, Food Hydrocolloids 10 (1996) 21-26]. The stress was calculated as:

$$\sigma = \frac{F}{A_0} \qquad (3)$$

where $\sigma$ is the stress (kPa), F is the force needed to burst the capsule (N) and $A_0$ is the cross-sectional area of the original liquid-core capsule ($mm^2$).

The engineering strain was calculated as:

$$\varepsilon_E = \frac{\Delta H}{H_0} \qquad (4)$$

where $\varepsilon_E$ is the engineering strain (–), $\Delta H$ is the total deformation (mm), and $H_0$ is the diameter of the original capsule (mm).

Presented results are averages of seven specimens from two different batches of each capsule type.

Capsule Regeneration

Capsule regeneration was carried out by suspending the capsules with the sorbed heavy metal in 1 M $HNO_3$ for 24 h [J. P. Ibáñez, Y. Umetsu, Potential of protonated alginate beads for heavy metals uptake, Hydrometallurgy 64 (2002) 89-99]. The capsules were then repeatedly washed with distilled water until a neutral pH was obtained. Adsorption capacity of the protonated capsules was measured as described above. The same capsules were regenerated three times. Presented results are averages of four different experiments.

Example 2—Effect of the Preparation Process Conditions on the Formation of Capsules The effect of different experimental conditions on the formation of the liquid alginate core capsules has been evaluated.

Effect of the Alginate Solution Concentration

The alginate solution concentration which was found to be the most suitable for the preparation of the capsules was 3% (w/w). Concentrations substantially higher than 3% (w/w) resulted in very viscous solutions which prevented complete and homogeneous dissolution of alginate. Lower concentrations reduced the heavy-metal ions adsorption ability of the capsules.

Effect of the Gellan Solution Concentration

The optimal concentration of the gellan solution was found to be 0.5% (w/w). Said concentration provided formation of essentially spherical liquid alginate core capsules. At the gellan solution concentrations of 0.2% (w/w) alginate drops penetrated the surface of the gellan solution, but a spherical capsule could not be produced. Instead alginate strips coated with gellan were formed. At the 1% (w/w) gellan solution concentration alginate drop could not penetrate the surface of gellan solution.

Effect of the $MgCl_2$ Concentration

Three different concentrations of magnesium chloride were tested: 0.25M, 0.5M and 1M. At the 0.25M concentration, non-spherical capsules were obtained. Furthermore, their mechanical strength was very low. Both 0.5M and 1M concentrations yielded spherical capsules, having 14.9 kPa and 15.2 kPa stress at failure, respectively. However, it is preferable to keep the concentration of magnesium ions as low as possible, to prevent extensive accumulation thereof in the capsule to minimize their potential interference with the adsorption and bonding of other cations.

Effect of the Alginate Solution Temperature

It was found that the alginate solution temperature has a prominent effect on the formation of capsules. The optimal temperature of the alginate solution for the formation of spherical capsules was found to be room temperature (i.e. about 25° C.). Below this temperature (for example at 10° C.), the formed capsules were not spherical and above this temperature (for example at 40° C.), alginate drops could not penetrate the gellan solution surface.

Effect of the Gellan Solution Temperature

The optimal temperature of the gellan solution was found to be 30° C. At lower temperatures gelling of the gellan solution was observed and above this temperature (for example at 40° C. and 50° C.) no capsules were formed and the solutions of alginate and gellan mixed together.

Example 3—Characterization of 0.5% Gellan and 3% Alginate Solutions

Before the capsules were produced, the physical properties of the 0.5% gellan solution used to create the outer membrane of the liquid-core capsule, and the 3% alginate solution that served as the liquid core, were measured (Table 1). The differences between the density and viscosity values of the two solutions ensured the formation of spherical liquid-core capsules (see further results), as previously reported for the formation of spherical liquid-core capsules containing oil surrounded by an alginate layer (Nussinovitch and Solomon, 1998).

TABLE 1

Characterization of gellan solution and alginate-$MgCl_2$ solution[†]

| Solution type | $\rho$ (g/cm$^3$) | $\eta$ (cP) | $\gamma$ (mN/m) |
|---|---|---|---|
| 0.5% (w/w) Gellan at 25° C. | 1.006$^a$ ± 0.030 | 8.9$^a$ ± 0.8 | 71.3$^a$ ± 0.2 |
| 3% (w/w) Alginate and 0.5 M $MgCl_2$ at 30° C. | 1.102$^b$ ± 0.053 | 694$^b$ ± 64 | 42.5$^b$ ± 2.5 |

[†]Each result is the average of at least seven determinations from two different batches ± SD. Different superscript letters in a column indicate significant differences at $P < 0.05$.

Example 4—Capsule Production

Alginate liquid-core capsules with a gellan membrane were produced in a one-step procedure by dropping a mixture of 3% (w/w) sodium alginate including 5% (w/w) (0.5 M) $MgCl_2$ salt into a 0.5% (w/w) gellan solution until a gellan-magnesium membrane formed as a result of diffusion of the magnesium cations into the gellan solution (FIG. 1). The gellan membrane was formed by reducing the electrostatic repulsion between gellan polysaccharides, allowing the positively charged magnesium to interact with the carboxyl group of the gellan (Morris et al., 2012). This type of capsule has never before been produced. Previously produced liquid-core capsules have consisted mainly of either an alginate membrane or a gellan membrane, but not both together, and the alginate has never been used in its non-crosslinked form. Lim and Sun (1980) were the first to describe a method for producing alginate-PLL liquid-core microcapsules to encapsulate pancreatic islets: they suspended the cells in a sodium-alginate solution and formed small spherical calcium-alginate beads by crosslinking with calcium salt, and then reacted them with PLL to create a PLL-alginate membrane around the bead. In the final stage, the bead's core, composed of calcium-alginate gel, was solubilized, thus forming liquid-core capsules containing cells [F. Lim, A. M. Sun, Microencapsulated islets as bioartificial endocrine pancreas, Science 210 (1980) 908-910]. Liquid-core capsules with a gellan membrane have also been produced [F. Alhaique, E. Santucci, M. Carafa, T. Coviello, E. Murtas, F. Riccieri, Gellan in sustained release formulations: preparation of gel capsules and release studies, Biomaterials 17 (1996) 1981-1986]: a mixture of $CaCl_2$, starch and a model drug was dropped into a 0.5% (w/w) gellan solution. The gellan gel membrane in that case was created by interaction between the gellan solution and the calcium cations that served as the crosslinkers.

Example 5—Characterization of the Capsules

The physical properties of the gellan-alginate capsules are presented in Table 2. In general, most of the parameters (Feret diameter, weight and membrane thickness) increased significantly with increasing duration of capsule membrane crosslinking. Aspect ratio values indicated that the capsules were close to a perfect sphere. Furthermore, there was no significant difference in the diameter of the entrapped alginate drop for the different capsules. FIG. 2 highlights the differences in the capsules formed after different crosslinking durations.

TABLE 2

Characterization of gellan-alginate capsules after different crosslinking durations[†]

| Duration of capsule membrane cross-linking (min) | Aspect ratio (—) | Feret diameter (mm) | Weight (mg) | Membrane thickness (μm) | Inside diameter (mm) |
|---|---|---|---|---|---|
| 0.5 | 0.93$^a$ ± 0.02 | 5.7$^a$ ± 0.3 | 123$^a$ ± 6 | 420$^a$ ± 11 | 3.9$^a$ ± 0.4 |
| 1.0 | 0.94$^a$ ± 0.02 | 6.2$^b$ ± 0.2 | 143$^b$ ± 7 | 625$^b$ ± 9 | 3.8$^a$ ± 0.2 |
| 1.5 | 0.94$^a$ ± 0.03 | 6.9$^c$ ± 0.2 | 173$^c$ ± 4 | 822$^c$ ± 21 | 3.8$^a$ ± 0.2 |
| 2.0 | 0.96$^a$ ± 0.02 | 7.4$^d$ ± 0.4 | 191$^d$ ± 4 | 977$^d$ ± 19 | 3.9$^a$ ± 0.3 |

[†]Each result is the average of at least seven determinations from two different batches ± SD. Different superscript letters in a column indicate significant differences at $P < 0.05$.

Example 6—Adsorption Efficiency of Lead Cations

Effect of Membrane Thickness

Adsorption efficiency of lead cations by the different capsules with different membrane thicknesses was examined. Four adsorption experiments were conducted for each capsule type: the first was performed after the capsule's production; the second one was performed immediately after the first adsorption experiment with the same capsule, and so on. Table 3 shows the adsorption capacities of the gellan-alginate capsules. The first adsorption experiment showed the highest adsorption capacity of the four experiments. Maximum adsorption was achieved after the fourth adsorption experiment in all capsule types (~300 mg Pb$^{2+}$/g alginate). The diffusion of lead cations inside the capsules was not uniform among the capsules in the first adsorption experiment: as membrane thickness decreased, the adsorption efficiency increased, probably due to improved diffusion through the membranes containing less gellan polymer.

TABLE 3

Adsorption capacity of lead cations (mg/g) by gellan-alginate capsules[†]

| Membrane thickness (μm) | Adsorption experiment no. | | | |
|---|---|---|---|---|
| | 1 | 2 | 3 | 4 |
| 420$^a$ ± 11 | 266.6$^a$ ± 8.3 | 28.0$^h$ ± 5.9 (295.6) | 17.7$^{ij}$ ± 4.7 (313.3) | 1.4$^f$ ± 1.7 (314.6) |
| 625$^b$ ± 9 | 221.1$^b$ ± 14.2 | 44.4$^g$ ± 2.9 (265.5) | 23.4$^{hi}$ ± 3.2 (288.9) | 6.7$^{lk}$ ± 2.5 (295.7) |
| 822$^c$ ± 21 | 211.7$^c$ ± 6.8 | 84.6$^f$ ± 6.2 (296) | 12.0$^{jk}$ ± 7.1 (308) | 2.6$^f$ ± 1.9 (311.0) |
| 977$^d$ ± 19 | 194.9$^d$ ± 15.4 | 94.0$^e$ ± 8.4 (288.9) | 15.3$^{ij}$ ± 4.1 (304) | 1.4$^f$ ± 1.2 (305.7) |

[†]Each result is the average of four determinations from four different batches ± SD. Different superscript letters in a column indicate significant differences at $P < 0.05$.

Effect of pH

Figure 3:
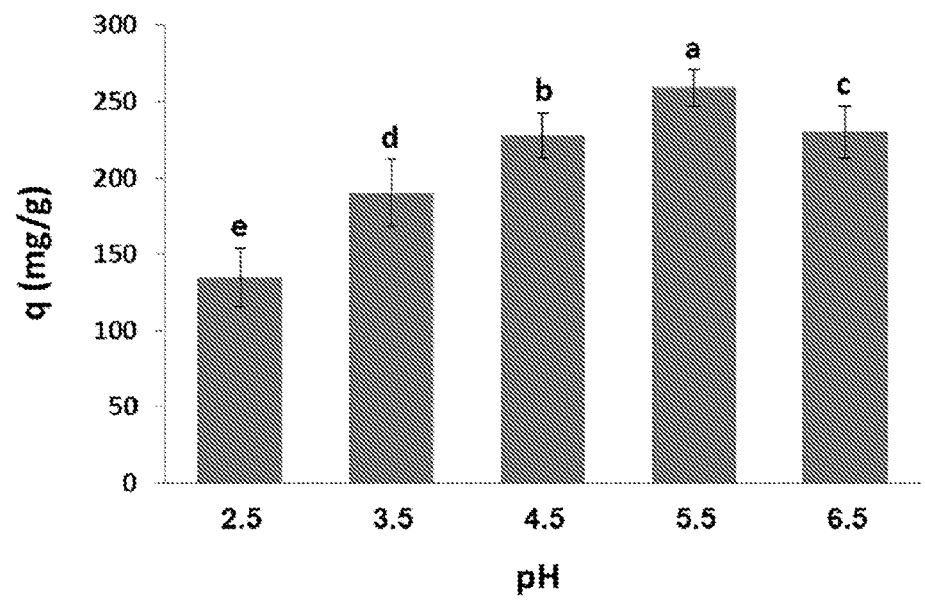
FIG. 3: pH effect on lead-adsorption efficiency (q) by gellan-alginate capsules. Each result is the average of four determinations from four different batches±SD. Different superscript letters indicate significant differences at $P<0.05$.

As previously observed, the adsorption of metal cations by alginate is mainly due to interaction between the metal cations and the alginate's carboxyl groups (Papageorgiou et al., 2006). In a similar fashion, the pH of the pollutant solution had a significant effect on the adsorption efficiency of gellan-alginate capsules (FIG. 3). The optimum pH for lead-cation adsorption was 5.5 (267 mg/g), while low adsorption was found at lower pH. At low pH values, the carboxyl groups of the gellan interact with protons (H$^+$) and the resultant repulsive forces restrict the approach of the metal ions. With increasing pH, the negative charge of the carboxyl groups is exposed and attraction between these negative charges and the metal cations increases the adsorption efficiency of the capsules. pH values higher than 6.5 were not examined due to possible precipitation of metal cations and hydroxyl salts.

Effect of Adsorption Time

Figure 4:
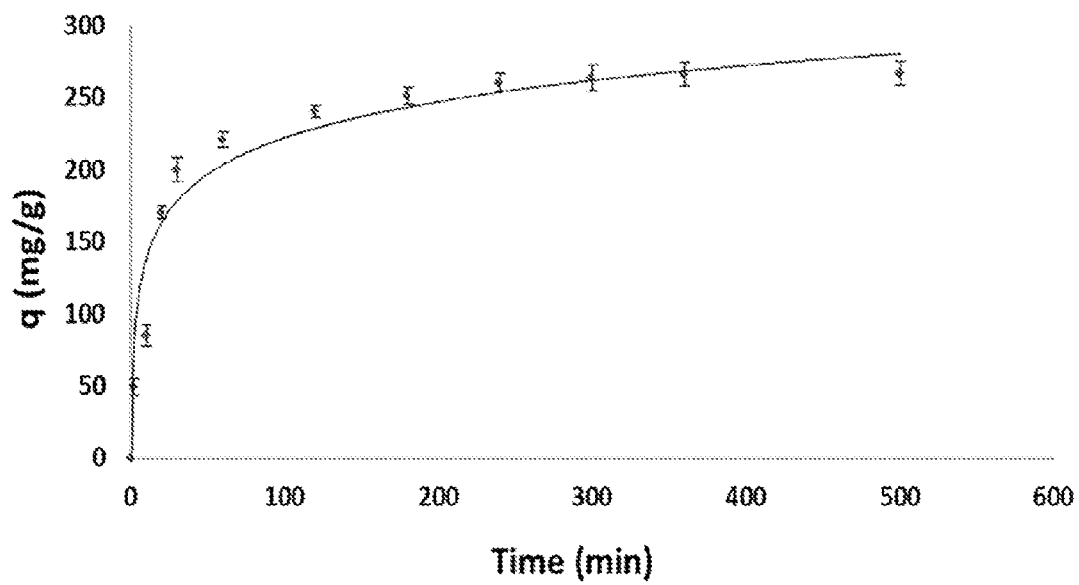
FIG. 4: Lead-adsorption efficiency (q) of gellan-alginate capsules during 500 min. Each result is the average of three determinations from three different batches±SD.

The adsorption efficiency for lead cations (estimated in mg Pb$^{2+}$/g alginate) during stirring was studied by mixing the novel capsules in a 1,000 ppm lead solution at pH 5.5 and 25° C. for 500 min. The results are shown in FIG. 4. Adsorption of lead cations by the gellan-alginate capsules occurred in two stages, as reported previously [F. A. A. Al-Rub, M. H. El-Naas, F. Benyahia, I. Ashour, Biosorption of nickel on blank alginate beads, free and immobilized algal cells, Process Biochem. 39 (2004) 1767-1773]: the first stage was rapid, with over 80% of the Pb$^{2+}$ being adsorbed within the first 60 min (220 mg/g); the second stage was slower, with the capsules adsorbing the remaining 20% of the Pb$^{2+}$ over 180 min (47 mg/g) until maximal lead-cation adsorption was reached.

Example 7—Mechanical Properties of the Gellan-Alginate Capsules

Before Adsorption

Figure 5:
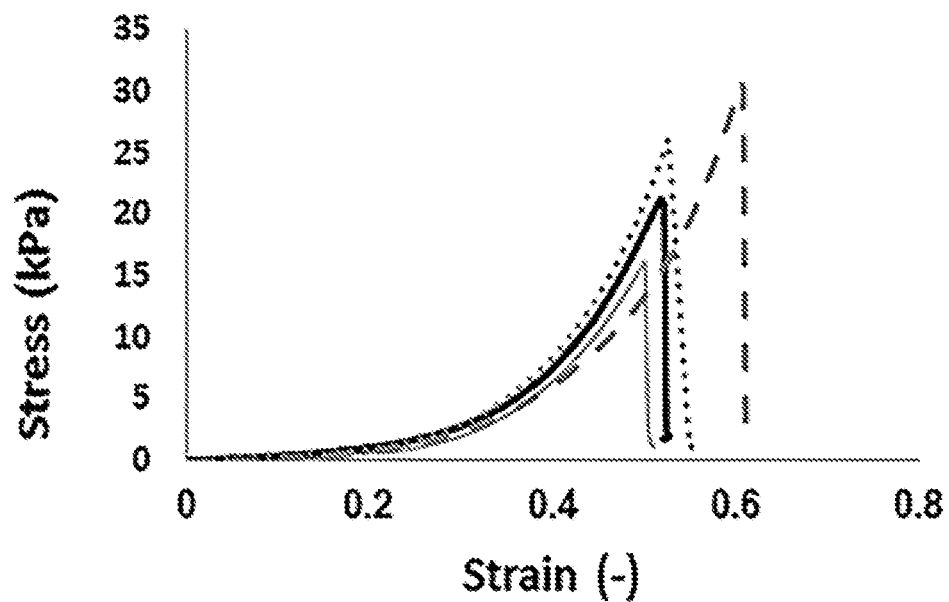
FIG. 5: Compressive stress-strain relationships for gellan-alginate liquid-core capsules with different membrane thicknesses (grey solid line represents 420 μm membrane, black solid line represents 625 μm membrane, dotted line represents 822 μm membrane, and dashed line represents 977 μm membrane).
Figure 6:
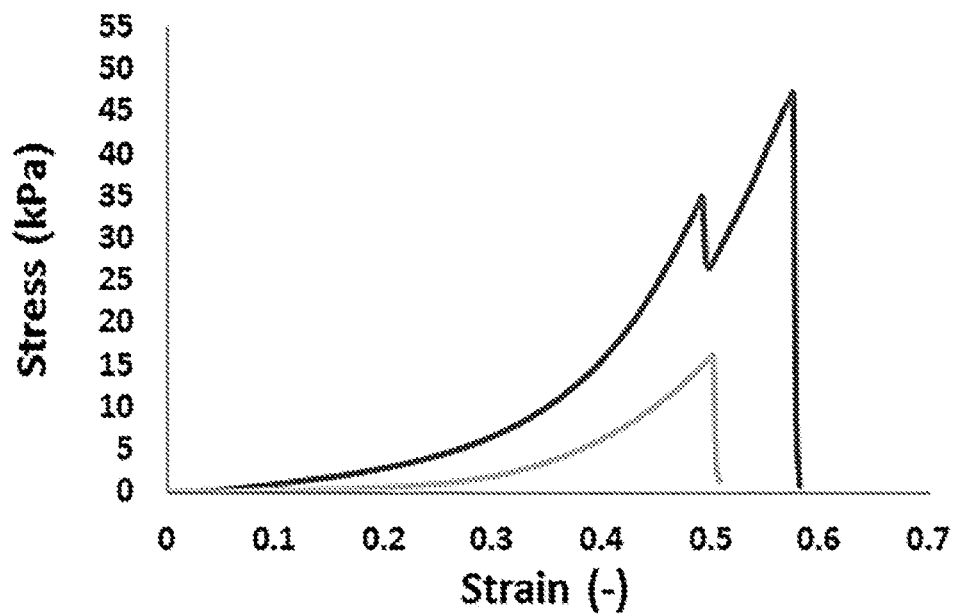
FIG. 6: Stress-strain relationships for gellan-alginate liquid-core capsules throughout compression, before and after lead-cation adsorption (black line—after adsorption, grey line—before adsorption).

Since the capsules were designed for inclusion in columns and were intended for industrial uses, the mechanical properties of the different liquid-core capsules before adsorption were studied by compression test. Typical stress-strain relationships of the compressed capsules before adsorption are shown in FIG. 5. The gellan-alginate capsules with membrane thickness of 977 μm presented the highest stress and strain values at failure (30.4±0.9 kPa and 0.59±0.03, respectively) compared to the capsules with thinner membranes: 822, 625 and 420 μm (stresses at failure: 24.6±1.1, 23.9±2.1 and 14.9±1.5 kPa, respectively; and strains at failure: 0.56±0.01, 0.54±0.02, 0.50±0.02, respectively). Thus the capsule with the thickest membrane was the most resistant to mechanical stresses and this liquid-core capsule was stronger and less brittle than the other three capsules. This was due to the longer crosslinking duration of the gellan membrane (2 min), allowing further interaction between the magnesium cations and the gellan's carboxyl groups After Adsorption The mechanical properties of the capsules changed as a result of the crosslinking of the alginate solution by the lead cations. After adsorption of the lead cations by the novel alginate-gellan liquid-core capsules, atypical stress-strain relationships were observed (FIG. 6). Two maxima were found during their compression. The first maximum was related to the stress at failure of the gellan membrane, and the second to the stress related to the yielding of the inner alginate gel which was created upon adsorption of the lead cations, and served as the inner core of the liquid-core capsules. In other words, before the adsorption, the gellan-alginate liquid-core capsule consisted of one gel matrix (gellan gel membrane) that held the alginate solution, but after lead-cation adsorption, the gellan-alginate capsules consisted of two gel matrices: the crosslinked alginate gel and the surrounding gellan membrane. After lead adsorption, the gellan membrane presented higher stress at failure, 35.9±4.2, relative to the gellan membrane before adsorption, 14.9±1.5. Nevertheless, no difference was found in the strain at failure values (Table 4). The difference between the stress values at failure was probably due to ion exchange of the magnesium cations for the lead ones because of latter's higher affinity for the gellan, creating a stronger gellan gel membrane [H. Grasdalen, O. Smidsrød, Gelation of gellan gum, Carbohydr. Polym. 7 (1987) 371-393].

TABLE 4

Stress and strain at failure of compressed gellan-alginate capsules before and after lead-cation adsorption[†]

| Capsule type | Broken matrix | Stress at failure (kPa) | Strain at failure (—) |
|---|---|---|---|
| Before adsorption | Gellan gel membrane | $14.9^a \pm 1.5$ | $0.50^a \pm 0.02$ |
| After adsorption | Gellan gel membrane | $35.9^b \pm 4.2$ | $0.51^a \pm 0.02$ |
|  | Alginate gel | $47.8^c \pm 3.5$ | $0.60^b \pm 0.03$ |

[†]Each result is the average of at least seven determinations from two different batches ± SD. Different superscript letters in a column indicate significant differences at $P < 0.05$.

Example 8—Improvement of Capsule Mechanical Properties

On the one hand, gellan-alginate capsules presented maximal adsorption when their membrane was thinnest (420 μm), but on the other, these capsules were weaker. Hence, three different reagents were used to strengthen the outer gellan membrane of the liquid-core capsules with 420 μm membrane thickness: $MgCl_2$, PLL and chitosan. Dissolution of $MgCl_2$ creates magnesium cations that interact with gellan's carboxyl groups. PLL and chitosan are polymers. When their pKa>pH, a polycation-polyanion interaction occurs between the negative charge of gellan's carboxyl groups and the positive charge of the amine groups. These interactions strengthen the gellan membrane. Table 5 shows the mechanical properties of the gellan-alginate capsules after strengthening. All three tested reagents strengthened the capsules significantly, but maximal strengthening was achieved with $MgCl_2$.

TABLE 5

Stress and strain at failure of compressed gellan-alginate capsules after membrane strengthening[†]

| Strengthening agent | Stress at failure (kPa) | Strain at failure (—) |
|---|---|---|
| None | $14.9^a \pm 1.5$ | $0.50^a \pm 0.02$ |
| 1.0% Chitosan | $24.9^b \pm 5.4$ | $0.53^a \pm 0.03$ |

TABLE 5-continued

Stress and strain at failure of compressed gellan-alginate capsules after membrane strengthening[†]

| Strengthening agent | Stress at failure (kPa) | Strain at failure (—) |
|---|---|---|
| 0.2% Poly-L-lysine | $22.2^b \pm 3.4$ | $0.52^a \pm 0.02$ |
| 5% $MgCl_2$ | $35.3^c \pm 5.9$ | $0.60^b \pm 0.03$ |

[†]Each result is the average of at least seven determinations from two different batches ± SD. Different superscript letters in a column indicate significant differences at $P < 0.05$.

Figure 7:
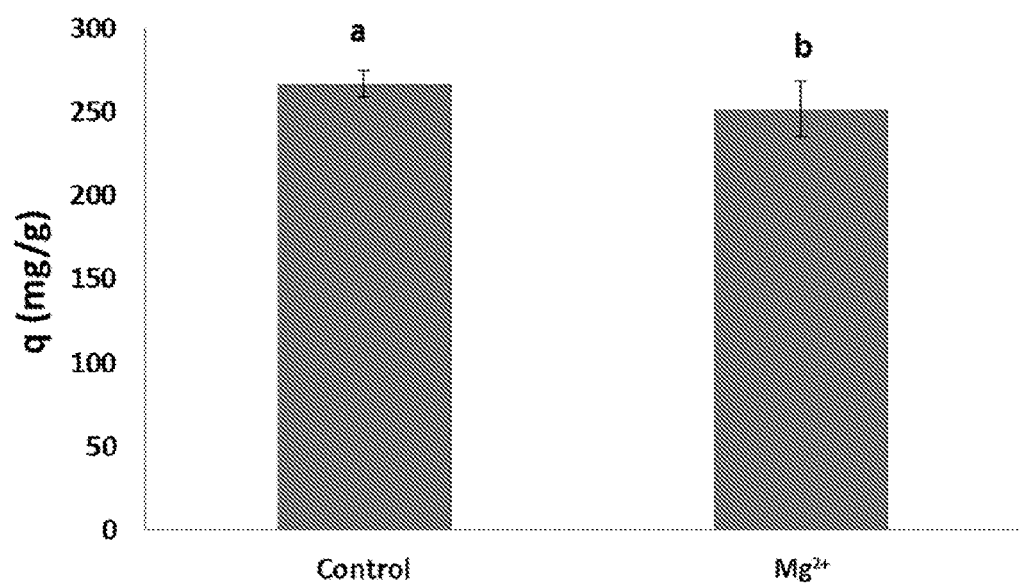
FIG. 7: Lead-adsorption efficiency (q) of gellan-alginate liquid-core capsules after membrane strengthening. Each result is the average of four determinations from four different batches±SD. Different superscript letters indicate significant differences at $P<0.05$.

Adsorption efficiency of the liquid-core $MgCl_2$-treated capsules was also tested. FIG. 7 shows that there was no significant difference between the adsorption efficiency of the strengthened and non-strengthened capsules (257 and 267 mg/g, respectively). It can be concluded that since magnesium cations have the lowest molecular weight among the reagents that were used to strengthen the capsules, they could diffuse more easily within the gellan matrix, further strengthening it. In contrast, the higher molecular weights of chitosan and PLL (polycations) presumably slowed their diffusion and limited their reaction with the gellan at the capsule surface.

Example 9—Improvement of Adsorption Efficiency

As noted hereinabove, the adsorption of lead cations improved with decreasing membrane thickness. Therefore, reduction of the capsule's membrane thickness was examined using the surfactant lecithin. Before capsule production, the physical properties of the gellan solution used to create the outer membrane of the liquid-core capsule were measured. Addition of lecithin to the 0.5% gellan solution reduced its surface tension, with no significant differences observed in the viscosities or densities of the tested liquids (Table 6).

TABLE 6

Characterization of 0.5% (w/w) gellan solution with and without lecithin at 30° C.[†]

| Solution type | (g/cm³) ρ | cP (η) | γ (mN/m) |
|---|---|---|---|
| Gellan | $1.006^a \pm 0.030$ | $8.9^a \pm 0.8$ | $71.3^a \pm 0.2$ |
| Gellan and lecithin | $1.012^a \pm 0.024$ | $9.2^a \pm 0.6$ | $45.4^b \pm 1.6$ |

[†]Each result is the average of four determinations from two different batches ± SD. Different Superscript letters in a column indicate significant differences at $P < 0.05$.

The physical properties of the gellan-alginate and lecithin-gellan-alginate capsules were compared (Table 7). The membrane thickness of the gellan-alginate capsules containing lecithin was reduced as a result of the better wetting ability of the gellan solution due to the reduction in surface tension, resulting in a membrane with less gellan polymer. Moreover, the Feret diameter and weight of a single capsule were also reduced after lecithin addition to the capsule's membrane. In contrast, the aspect ratio and inside diameter of the included alginate core remained similar.

TABLE 7

Characterization of gellan-alginate capsules with and without lecithin addition[†]

| Capsule type | Aspect ratio (—) | Feret diameter (mm) | Weight (mg) | Membrane thickness (μm) | Inside diameter (mm) |
|---|---|---|---|---|---|
| Gellan-alginate | $0.95^a \pm 0.03$ | $5.71^a \pm 0.31$ | $123^a \pm 6$ | $420^a \pm 11$ | $3.9^a \pm 0.4$ |
| Gellan-alginate-lecithin | $0.93^a \pm 0.02$ | $5.32^b \pm 0.05$ | $102^b \pm 9$ | $353^b \pm 20$ | $3.8^a \pm 0.3$ |

[†]Each result is the average of at least seven determinations from two different batches ± SD. Different superscript letters in a column indicate significant differences at $P < 0.05$.

Figure 8:
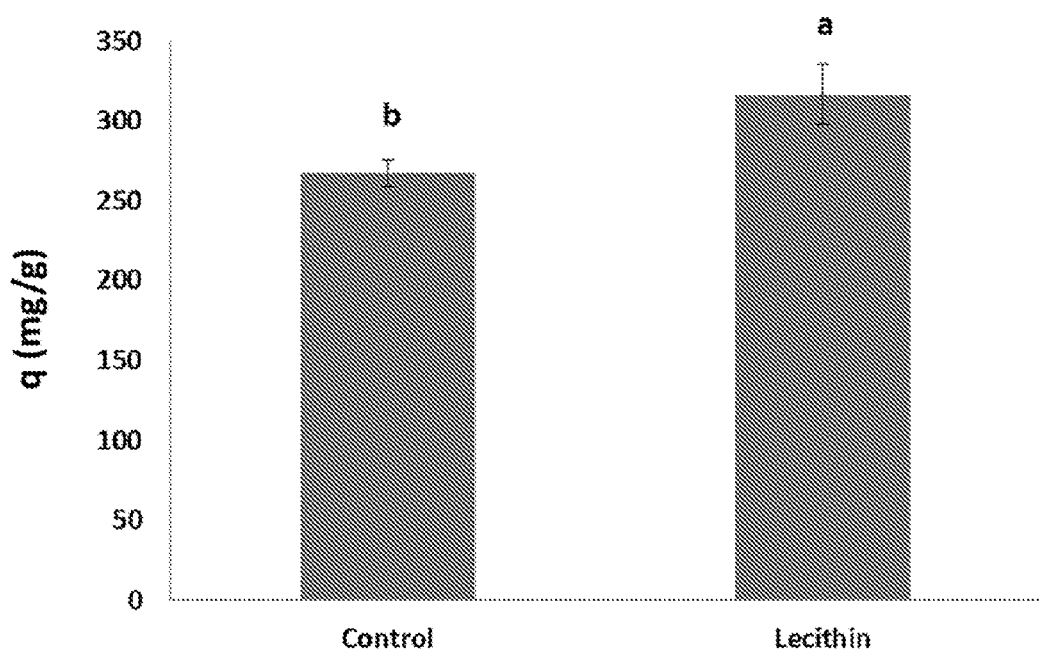
FIG. 8: Lead-adsorption efficiency (q) of gellan-alginate capsules after lecithin addition. Each result is the average of four determinations from four different batches±SD. Different superscript letters indicate significant differences at $P<0.05$

Lecithin inclusion in the gellan also influenced the adsorption process of the formed liquid-core capsules. In adsorption experiments (FIG. 8), the lead-adsorption efficiency of the gellan-alginate liquid-core capsules was improved from 267 to 316 mg $Pb^{2+}$/g, most likely due to the thinner membrane and improved mass transfer.

The mechanical properties of the gellan-alginate capsules with and without lecithin are presented in Table 8. No significant differences were found between the values of stress and strain at failure for these capsules. Despite its negative charge, lecithin had no impact on capsule strength because of the small amount added (20 ppm). Moreover, after production, the capsules were washed to remove the residual lecithin, so that it could not bond to the gellan membrane and further strengthen it.

TABLE 8

Stress and strain at failure of compressed gellan-alginate capsules with and without lecithin addition[†]

| Capsule type | Stress at failure (kPa) | Strain at failure (—) |
| --- | --- | --- |
| Gellan-alginate | $14.9^a \pm 1.5$ | $0.50^a \pm 0.02$ |
| Gellan-alginate-lecithin | $12.9^a \pm 2.3$ | $0.49^a \pm 0.02$ |

[†]Each result is the average of at least seven determinations from two different batches ± SD. Different superscript letters in a column indicate significant differences at $P < 0.05$.

Example 10—Combined Capsules

Figure 9:
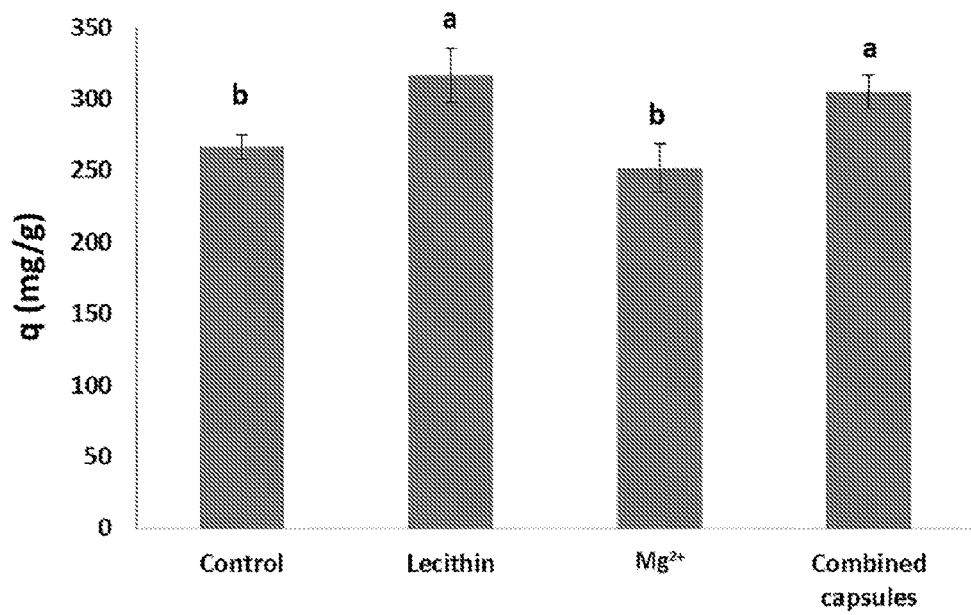
FIG. 9: Lead-adsorption efficiency (q) of gellan-alginate capsules after lecithin addition (lecithin), after external strengthening with magnesium cations ($Mg2+$), and after treatment with magnesium cations and lecithin (combined capsules) in comparison to untreated capsules (control). Each result is the average of four determinations from four different batches±SD. Different superscript letters indicate significant differences at $P<0.05$.

To obtain gellan-alginate liquid-core capsules with high adsorption efficiency and concomitantly suitable mechanical properties, it was decided to further manipulate the properties of the gellan membrane. Lecithin addition targeted to the reducing of the membrane thickness was combined with subsequent immersion in $MgCl_2$ solution for external strengthening of the capsule membrane. Lead-adsorption efficiency was measured for four different types of liquid-core gellan-alginate capsules: with lecithin, with $MgCl_2$, combined capsules (with $MgCl_2$ and lecithin) and no treatment (controls). The results are presented in FIG. 9. Capsules with lecithin addition and combined capsules showed maximum lead adsorption (316 and 305 mg/g, respectively), whereas capsules with $MgCl_2$ addition and control capsules showed minimum lead adsorption (252 and 267 mg/g, respectively).

While testing the mechanical properties of the capsules it was noticed that upon compression (Table 9), both the combined capsules and capsules after external strengthening by magnesium cation diffusion had higher stresses at failure (32.4±4.6 and 35.3±5.9, respectively) than the control capsules (with no treatment) and capsules with lecithin addition to the membrane (14.9±1.5 and 12.9±2.3, respectively).

It was concluded that incorporating lecithin into the gellan membrane of the gellan-alginate capsules, and secondary treatment with $MgCl_2$ for external strengthening, produce highly efficient adsorption capacity and mechanically strong capsules.

TABLE 9

Stress and strain at failure of compressed gellan-alginate capsules after lecithin addition (lecithin), after external strengthening with magnesium cations ($Mg^{2+}$), after treatment with magnesium cations and lecithin (combined capsules) in comparison to untreated capsules (control)[†]

| Capsule type | Stress at failure (kPa) | Strain at failure (—) |
| --- | --- | --- |
| Control | $14.9^a \pm 1.5$ | $0.50^a \pm 0.02$ |
| Lecithin | $12.9^a \pm 2.3$ | $0.49^a \pm 0.02$ |
| $Mg^{2+}$ | $35.3^b \pm 5.9$ | $0.56^b \pm 0.03$ |
| Combined capsules | $32.4^b \pm 4.6$ | $0.52^{ab} \pm 0.05$ |

[†]Each result is the average of at least seven determinations from two different batches ± SD. Different superscript letters in a column indicate significant differences at $P < 0.05$.

Example 11—Capsule Regeneration

Figure 10:
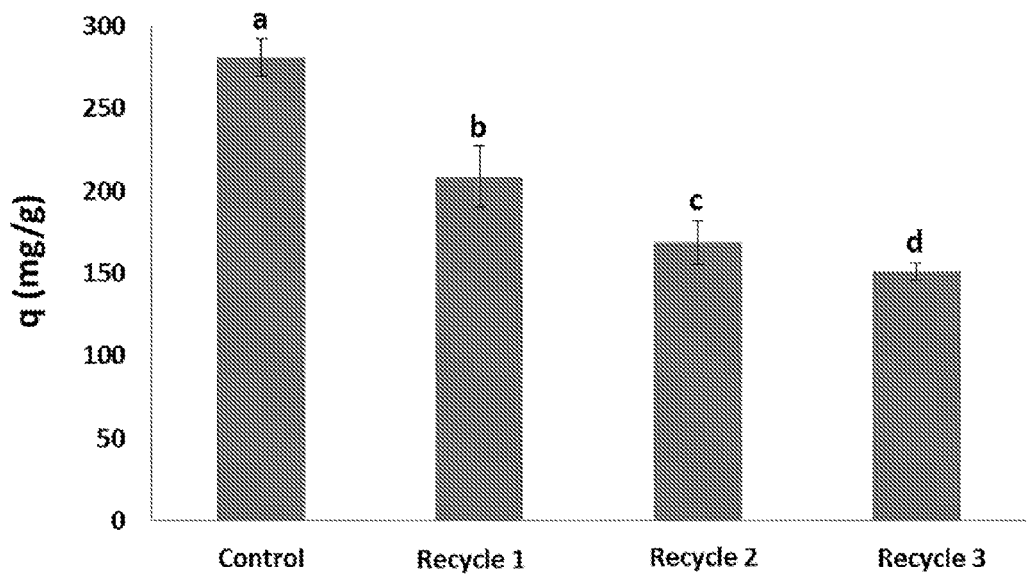
FIG. 10: Lead-adsorption efficiency (q) of gellan-alginate capsules after each of three regeneration cycles. Each result is the average of four determinations from four different batches±SD. Different superscript letters indicate significant differences at $P<0.05$.

Capsule regeneration for subsequent reuse is of great importance both economically and environmentally. Capsule reuse is cost-effective and environmentally friendly, giving it an obvious advantage over conventional heavy-metal removal methods. The regenerative ability of gellan-alginate liquid-core capsules was examined by exposing the capsules after adsorption to highly concentrated strong acid ($HNO_3$), in order to replace the adsorbed metal cations with protons. This method has been described previously to increase the adsorption capacity of beads [R. Lagoa, J. Rodrigues, and Evaluation of dry protonated calcium alginate beads for biosorption applications and studies of lead uptake, Appl. Biochem. Biotechnol. 143 (2007) 115-128]: the adsorption capacity for lead cations was tested using calcium-alginate beads and calcium-alginate beads after protonation with $HNO_3$. The protonation was intended to increase bead adsorption capacity by generating carboxylic groups with labile protons suitable for exchange with metal ions. The protonated beads were found to have a larger binding capacity for lead cations than the non-protonated beads (160 and 130 mg $Pb^{2+}$/g dry alginate, respectively). FIG. 10 shows the amount of lead cation adsorbed by capsules after one, two and three regeneration cycles. In general, the capsules had high regenerative ability but after every reuse, the capsules showed significant loss of adsorption capacity. The amount of lead cations adsorbed after the first regeneration process was 209 mg $Pb^{2+}$/g alginate, 168 mg $Pb^{2+}$/g alginate after the second regeneration and 151 mg $Pb^{2+}$/g alginate after the third and last regeneration. Regeneration of the capsules could be attributed to ion exchange. Protons from the $HNO_3$ replaced the carboxyl-bound cations in the alginate gel, thus restoring the capsule's function due to better affinity of metal cations to the alginate than protons [J. P. Ibánez, Y. Umetsu, Potential of protonated alginate beads for heavy metals uptake, Hydrometallurgy 64 (2002) 89-99]. Regenerated capsules contained less contaminant cations, but were weaker than the capsules before protonation (stress at failure, Table 10). Hence, a secondary treatment with $MgCl_2$ was necessary to strengthen the capsule membrane before reuse (Table 10). The capsules could be regenerated three times before they showed damage from the oxidizing properties of the $HNO_3$. The carboxylic group is highly resistant to oxidation, explaining why the capsules lasted as long as they did.

TABLE 10

Stress and strain at failure of compressed gellan-alginate capsules after protonation, and after protonation and strengthening with magnesium chloride in comparison to capsules with no treatment[†]

| Treatment | Broken matrix | Stress at failure (kPa) | Strain at failure (—) |
|---|---|---|---|
| None | Gellan gel membrane | $35.9^b \pm 4.2$ | $0.51^b \pm 0.03$ |
|  | Alginate gel | $47.8^a \pm 3.5$ | $0.59^a \pm 0.03$ |
| Protonation | Gellan gel membrane | $6.8^e \pm 0.5$ | $0.34^e \pm 0.02$ |
|  | Alginate gel | $9.6^d \pm 0.8$ | $0.43^c \pm 0.02$ |
| Protonation and strengthening | Gellan gel membrane | $21.3^c \pm 4.1$ | $0.51^b \pm 0.03$ |
|  | Alginate gel | $82^d \pm 1.6$ | $0.40^d \pm 0.03$ |

[†]Each result is the average of at least seven determinations from two different batches ± SD. Different superscript letters indicate significant differences at $P < 0.05$.

Example 12—Adsorption of Additional Metal Ions

Figure 11:
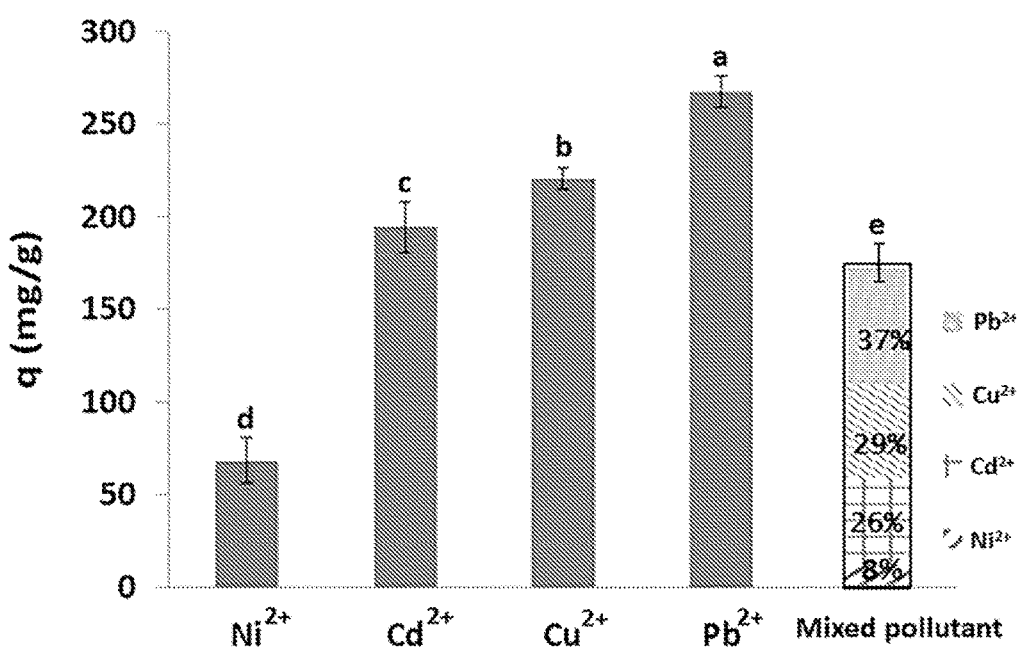
FIG. 11: Efficiency of adsorption (q) of different metal cations and a mixed pollutant by gellan-alginate capsules. Each result is the average of four determinations from four different batches±SD. Different superscript letters indicate significant differences at $P<0.05$. Mixed pollutant is represented by the right-most column, which includes (from bottom to top): $Ni^{2+}$ (8% adsorption efficiency), $Cd^{2+}$ (26% adsorption efficiency), $Cu^{2+}$ (29% adsorption efficiency), and $Pb^{2+}$ (37% adsorption efficiency).

Normally contaminated water contains not just lead cations, but also other cations or combinations of different cations. Therefore, further experiments were performed to test the gellan-alginate liquid-core capsules' ability to adsorb other heavy metal cations from single-metal and multiple-metal solutions. Adsorption efficiency of the capsules for other metals is shown in FIG. 11. Adsorption efficiency for lead cations was 267 mg/g, for copper cations, 219 mg/g, for cadmium cations 197 mg/g and for nickel cations 65 mg/g. There were marked differences between the adsorption capacities of the gellan-alginate capsules for the different metals examined, following the order: $Pb^{2+}>Cu^{2+}>Cd^{2+}>Ni^{2+}$. This order was found to be correlated with the affinity of the cations to the alginate carboxyl groups—as the affinity increased, so did the treatment's efficiency. Moreover, adsorption capacity of the multiple-metal solution was lower (172 mg/g) than that of the single-metal solutions of lead and copper, probably due to interference by the metals with low affinity to alginate, as reported in a previous study in which the presence of magnesium cations (having low affinity for the alginate) inhibited the crosslinking process of alginates by other cations (having high affinity to the alginate) [N. Fatin-Rouge, A. Dupont, A. Vidonne, J. Dejeu, P. Fievet, A. Foissy, Removal of some divalent cations from water by membrane-filtration assisted with alginate, Water Res. 40 (2006) 1303-1309].

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A hydrocolloid core-shell capsule comprising:
   a liquid core comprising a non-crosslinked alginate solution; and
   a solid or semi-solid shell comprising a hydrocolloid other than alginate crosslinked with metal ions, which do not crosslink alginate.

2. The capsule according to claim 1, wherein the metal ions are selected from the group consisting of magnesium ions, potassium ions and sodium ions.

3. The capsule according to claim 2, wherein the ions are magnesium ions, and the concentration of the magnesium ions ranges from about 0.075 mM/g(hydrocolloid) to about 0.5 mM/g(hydrocolloid).

4. The capsule according to claim 1, wherein the concentration of the alginate solution ranges from about 1% (w/w) to about 10% (w/w).

5. The capsule according to claim 1, wherein the alginate solution has a concentration of calcium ions that is lower than about 0.01M.

6. The capsule according to claim 1, wherein the shell hydrocolloid is selected from gellan or k-carrageenan.

7. The capsule according to claim 1, wherein the shell further comprises at least one surfactant selected from the group consisting of lecithin, sultaines CHAPS, cocamidopropyl hydroxysultaine, cocamidopropyl betaine, phosphatidylserine, phosphatidylethanolamine, phosphatidylcholine, sphingomyelin and combinations thereof.

8. The capsule according to claim 1, wherein the shell further comprises a polycation selected from the group consisting of poly-L-lysine (PLL), polyarginine, chitosan, and combinations thereof.

9. The capsule according to claim 1, wherein the aspect ratio of the capsule ranges from about 0.90 to about 1, and/or the diameter of the capsule ranges from about 50 μm to about 5 cm, and/or the volume of the alginate solution ranges from about 100 microliter to about 1 ml.

10. The capsule according to claim 1, wherein the shell thickness ranges from about 0.2 mm to about 1.2 mm.

11. A method for the preparation of the hydrocolloid core-shell capsule according to claim 1, the method comprising:
   (i) preparing a mixture of alginate ions and metal ions, which do not crosslink alginate and crosslink said hydrocolloid;
   (ii) providing a hydrocolloid solution, wherein the hydrocolloid is other than alginate;
   (iii) dripping the mixture of the metal ions and alginate ions into the hydrocolloid solution under constant mixing; and
   (iv) suspending the mixture formed in step (iii), thereby forming the hydrocolloid core-shell capsules.

12. The method according to claim 11, wherein the dripping in step (iii) is performed at a rate ranging from about 0.25 ml/sec to about 30 ml/sec, and/or wherein the mixture is suspended in step (iv) for from about 0.1 to about 5 minutes.

13. The method according to claim 11, wherein the mixture of alginate ions and metal ions comprises alginate salt or alginic acid ester in a weight percent ranging from about 1% to about 10% of the total weight of the mixture, and/or the hydrocolloid is present in the hydrocolloid solution in a weight percent of from about 0.25% to about 0.75% of the total weight of the solution.

14. The method according to claim 11, wherein mixture of alginate ions and metal ions comprises magnesium salt in the molar concentration of from about 0.25M to about 1.5M.

15. The method according to claim 11, wherein the density of the mixture of alginate ions and metal ions ranges from about 1.05 g/cm³ to about 1.16 g/cm³ and the density of the hydrocolloid solution ranges from about 0.96 g/cm³ to about 1.04 g/cm³, and/or wherein the viscosity of the mixture of alginate ions and magnesium ions ranges from about 600 to about 800 cP at 6.5 1/sec shear rate and temperature of 25° C. and the viscosity of the hydrocolloid solution ranges from about 5 to about 15 cP at 6.5 1/sec shear rate and temperature of 30° C.

16. The method according to claim 11, wherein in step (ii) the hydrocolloid solution comprises a surfactant.

17. The method according to claim 11, comprising an additional step (v) comprising contacting the capsules with a cross linking agent or with a polycation.

18. A device comprising a plurality of capsules according to claim 1, wherein the plurality of capsules is immobilized within said device, said immobilization enabling flow of a liquid through the device.

19. A method of removal of heavy metal ions from a liquid-containing environment, the method comprising bringing the device of claim 18 in contact with the liquid-containing environment to entrap the heavy metal ions into the plurality of capsules.

20. The method according to claim 19, wherein the heavy metal ion is selected from the group consisting of chromium, cobalt, nickel, copper, zinc, arsenic, selenium, silver, cadmium, antimony, mercury, thallium, lead ions and combinations thereof.

* * * * *